(12) United States Patent
Wallach

(10) Patent No.: US 12,213,803 B2
(45) Date of Patent: *Feb. 4, 2025

(54) BREATHING BIOFEEDBACK DEVICE

(71) Applicant: Orna Levin, Kfar Netter (IL)

(72) Inventor: Adi Wallach, Kfar Netter (IL)

(73) Assignee: Orna Levin, Kfar Netter (IL)

(*) Notice: Subject to any disclaimer, the term of this patent is extended or adjusted under 35 U.S.C. 154(b) by 0 days.

This patent is subject to a terminal disclaimer.

(21) Appl. No.: 18/216,477

(22) Filed: Jun. 29, 2023

(65) Prior Publication Data
US 2023/0337974 A1    Oct. 26, 2023

Related U.S. Application Data

(63) Continuation of application No. 17/533,701, filed on Nov. 23, 2021, now Pat. No. 11,730,423, which is a (Continued)

(30) Foreign Application Priority Data

Nov. 21, 2011    (GB) ..................................... 1120060

(51) Int. Cl.
*A61B 5/087*    (2006.01)
*A61B 5/00*    (2006.01)
(Continued)

(52) U.S. Cl.
CPC ............. *A61B 5/486* (2013.01); *A61B 5/087* (2013.01); *A61B 5/097* (2013.01); *A61B 5/4839* (2013.01); *A61B 5/7405* (2013.01); *A61B 5/742* (2013.01); *A61B 5/7455* (2013.01); *A61K 36/00* (2013.01); *A61M 15/08* (2013.01); *A61M 21/02* (2013.01); *A63B 23/185* (2013.01); *A63B 24/0087* (2013.01); *A61B 5/0873* (2013.01); *A61B 5/0875* (2013.01); *A61B 5/0876* (2013.01); *A61B 5/0878* (2013.01); *A61B 5/09* (2013.01); (Continued)

(58) Field of Classification Search
CPC ..... A61B 5/087; A61B 5/0873; A61B 5/0875; A61B 5/0876; A61B 5/0878; A61B 5/09; A61B 5/097; A61B 5/4839; A61B 5/486; A61B 5/7405; A61B 5/742; A61B 5/7455; A61K 36/00; A61M 15/08; A61M 2016/0024; A61M 2021/0016; A61M 21/02; A61M 2205/3334; A61M 2205/502; A61M 2205/583; A61M 2205/8206; A61M 2205/825; A61M 15/00; A63B 2024/0065; A63B 2024/0068; A63B 2220/805; A63B 2220/833; A63B 2230/405; A63B 2230/435; A63B 2230/505; A63B 23/185; A63B 24/0087

See application file for complete search history.

(56) References Cited

U.S. PATENT DOCUMENTS 6,190,326 B1*    2/2001   McKinnon ............. A61B 5/411
                                                           600/300
6,626,843 B2*    9/2003   Hillsman ............. A63B 23/185
                                                           600/529
2013/0066225 A1* 3/2013   Kojouri .................. A61B 5/091
                                                           600/538

* cited by examiner

*Primary Examiner* — Eric J Messersmith
(74) *Attorney, Agent, or Firm* — Fresh IP PLC; Clifford D. Hyra; Aubrey Y. Chen

(57) ABSTRACT

Disclosed are biofeedback methods and devices suitable for providing biofeedback useful for helping a user control an own breathing, for example, to help in inducing deep breathing, and such biofeedback devices further comprising a dispenser for dispensing an inhalable substance.

18 Claims, 13 Drawing Sheets

Related U.S. Application Data continuation of application No. 17/504,540, filed on Oct. 19, 2021, now Pat. No. 11,717,215, which is a continuation of application No. 15/708,189, filed on Sep. 19, 2017, now Pat. No. 11,179,101, which is a continuation of application No. 14/353,646, filed as application No. PCT/IB2012/056574 on Nov. 20, 2012, now abandoned.

(51) Int. Cl.
| | |
|---|---|
| *A61B 5/097* | (2006.01) |
| *A61K 36/00* | (2006.01) |
| *A61M 15/08* | (2006.01) |
| *A61M 21/02* | (2006.01) |
| *A63B 23/18* | (2006.01) |
| *A63B 24/00* | (2006.01) |
| *A61B 5/09* | (2006.01) |
| *A61M 16/00* | (2006.01) |
| *A61M 21/00* | (2006.01) |

(52) U.S. Cl.
CPC ............... *A61M 2016/0024* (2013.01); *A61M 2021/0016* (2013.01); *A61M 2205/3334* (2013.01); *A61M 2205/502* (2013.01); *A61M 2205/583* (2013.01); *A61M 2205/8206* (2013.01); *A61M 2205/825* (2013.01); *A63B 2024/0065* (2013.01); *A63B 2024/0068* (2013.01); *A63B 2220/805* (2013.01); *A63B 2220/833* (2013.01); *A63B 2230/405* (2013.01); *A63B 2230/435* (2013.01); *A63B 2230/505* (2013.01)

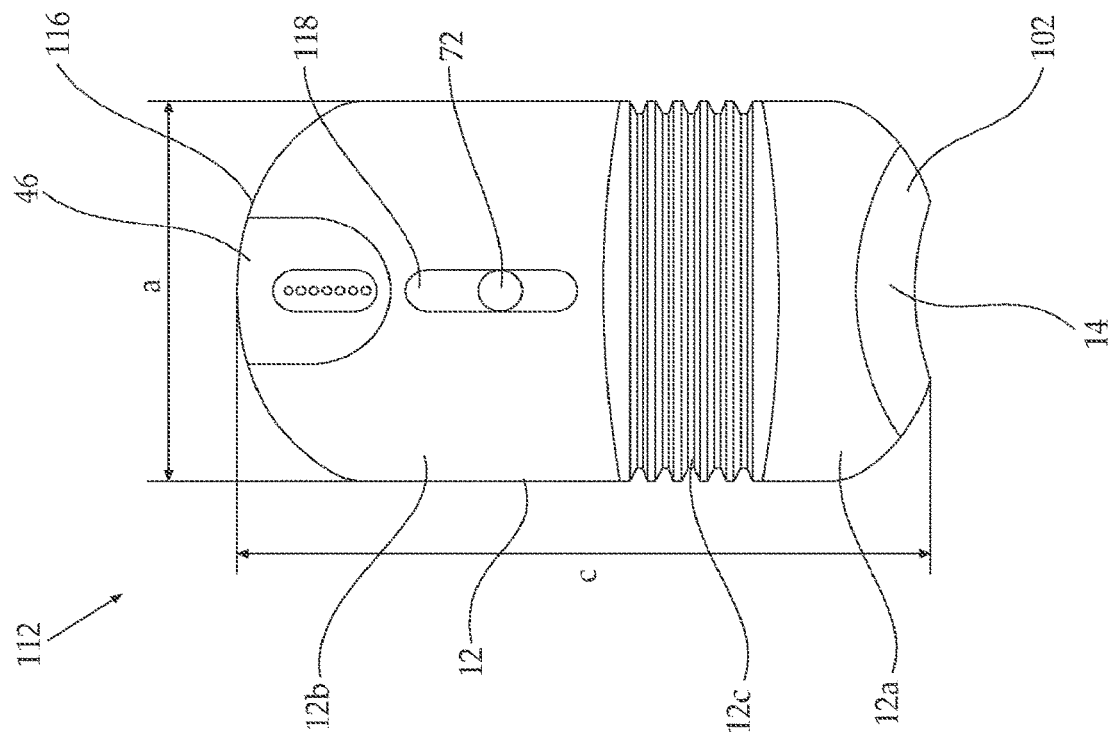
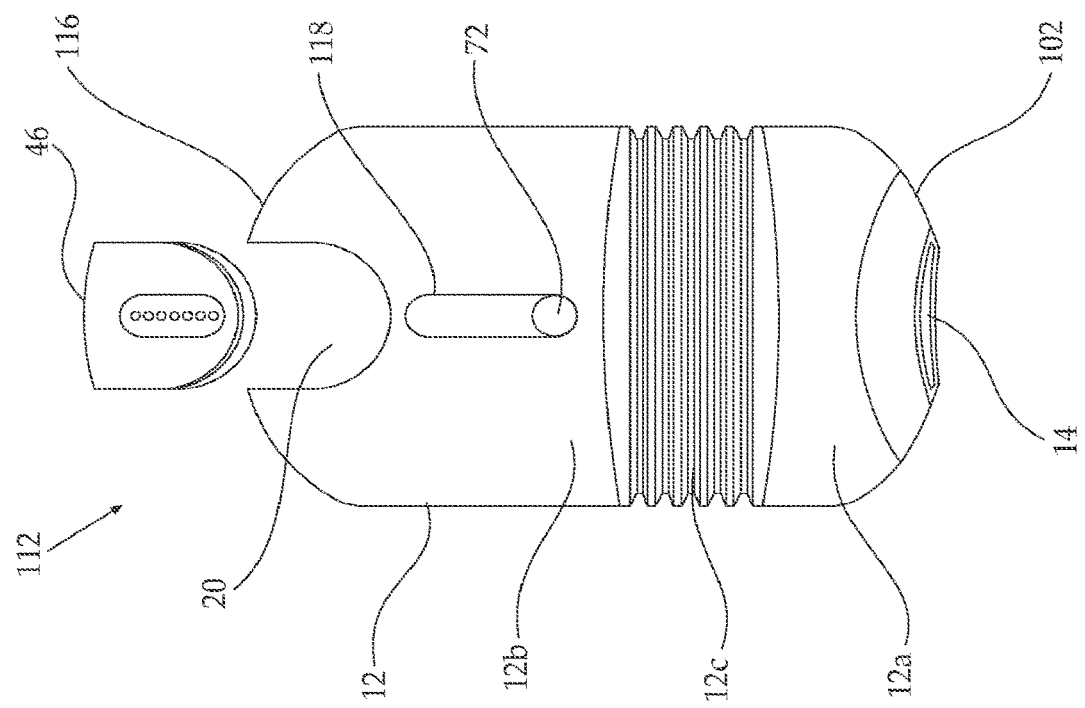

BREATHING BIOFEEDBACK DEVICE

RELATED APPLICATION

This application is a continuation of U.S. patent application Ser. No. 17/533,701, filed on Nov. 21, 2021, which is a continuation of U.S. patent application Ser. No. 17/504,540, filed on Oct. 19, 2021, which is a continuation of U.S. patent application Ser. No. 15/708,189, filed on Sep. 19, 2017, which is a continuation of U.S. patent application Ser. No. 14/353,646, filed on Apr. 23, 2014, which is a 371 of PCT/IB2012/056574, filed on Nov. 20, 2012 and claims priority from UK Patent Application No. GB1120060.7 filed 21 Nov. 2011, each of which is incorporated by reference as if fully set-forth herein.

FIELD AND BACKGROUND OF THE INVENTION

The invention, in some embodiments, relates to the field of biofeedback, and more particularly, but not exclusively, to methods and devices suitable for providing biofeedback useful for helping a user control an own breathing, for example, to help in inducing deep breathing.

Breathing is the process by which animals take in oxygen necessary for cellular metabolism and release the carbon dioxide that accumulates in the body as a result of the expenditure of energy.

Breathing can be affected by conditions such as emotional state (such as stress, excitement, fear, etc.), physical exercise, temperature, ingested or inhaled substances weather and environmental conditions, various diseases, and obesity.

The breathing pattern of an individual changes under stress. Typically, a stressed individual takes small, shallow breaths, using the shoulders rather than the diaphragm to move air in and out of the lungs. This style of breathing removes too much carbon dioxide from the blood, leading to hyperventilation, which can prolong feelings of anxiety by exacerbating physical symptoms of stress, including chest tightness, constant fatigue, faintness and lightheadedness, feelings of panic, headaches, heart palpitations, insomnia, muscular aches, twitches or stiffness.

Breathing is one of the few bodily functions that can be controlled, within limits, both consciously and unconsciously. Conscious control of breathing is provided by the autonomic nervous system via the cerebral cortex. Conscious control of breathing is common in many forms of meditation, such as forms of yoga, and controlled, deep, breathing from the abdomen rather than from the upper chest, has been found to induce relaxation, leading to lowered blood pressure and heart rate, reduced amounts of stress hormones, reduced lactic acid build-up in muscle tissue, balanced levels of oxygen and carbon dioxide in the blood, improved immune system functioning, increased physical energy and feelings of calm and well-being. The use of slow, deep breathing, particularly deep abdominal breathing as a means of promoting relaxation is considered to be of help in managing stress, as well as a range of disorders which are related to, or affected by stress including anxiety, asthma, chronic fatigue syndrome, chronic pain, high blood pressure, insomnia, panic attacks, labor pain, and some skin conditions such as eczema, and as well as various psychosomatic and psychoneurotic disorders.

In relaxed, deep breathing, the respiration rate is preferably slow (less than 8 breaths per minute), with large tidal volume (at least 2000 ml) and smooth flow rates, predominant abdominal expansion during inhalation and abdominal contraction during exhalation. The exhalation duration is significantly longer than the inhalation time and the end-tidal $CO_2$ is around 5%. Preferably for relaxation inhalation is through the nose and exhalation is prolonged, slow and through the mouth.

Various biofeedback techniques and systems have been proposed to assist a user in achieving controlled breathing.

The Respiratory Biofeedback Device produced by Bio-Mental mBh (Vierlinden, Germany) detects respiratory movement by means of a sensor worn by the user and converts the detected movement to an optical and/or acoustic signal that makes the user aware of the own breathing rhythm and respiratory rate. The device includes a feedback mask and breath sensor.

US Patent Publication US2010/0240945 discloses respiratory biofeedback devices and methods which include producing a signal in response to a user's respiratory activity by acquiring sounds of a user's breathing.

Publications that provide background for understanding the field of the invention include US Patent Publications US2007/167855, US2011/021940; US2012/029376; U.S. Pat. Nos. 4,984,158; 5,357,975; 6,165,105; PCT publication WO2007/012818; UK Patent application GB2480605; and Japan patent application JP201004457. It is important to note that at least some of the references were published after the priority date of the instant application.

SUMMARY OF THE INVENTION

Some embodiments of the invention relate to methods and biofeedback devices useful for helping a user control an own breathing. In some embodiments, a signal related to a determined exhalation duration is reported to the user as biofeedback. The biofeedback makes the user aware if breathing is too shallow and helps the user increase exhalation duration, in some embodiments helping to induce deep breathing.

According to some embodiments of the invention, there is provided a biofeedback device for providing biofeedback useful for helping a user control breathing, the device comprising a housing configured to be hand-held by the user; an exhalation inlet for receiving exhaled breath of the user; physically associated with the housing, an exhalation determiner functionally associated with the exhalation inlet, configured to determine when exhaled breath is received by the exhalation inlet; and a reporter associated with the exhalation determiner, the reporter configured to provide a signal related to an exhalation duration of the exhaled breath received from the exhalation determiner to the user.

According to some embodiments of the invention, there is also provided a biofeedback device for providing biofeedback useful for helping a user control breathing, the device comprising:

a housing configured to be hand-held by the user;

an exhalation inlet for receiving exhaled breath from the mouth of the user;

physically associated with the housing, an inhalable substance outlet and a functionally-associated dispenser configured for dispensing an inhalable substance to the user through the inhalable substance outlet, wherein the housing is configured so that when the exhalation inlet is positioned for the receiving the exhaled breath from the mouth, the inhalable substance outlet is located in proximity of the nostrils of the user;

physically associated with the housing, an exhalation determiner functionally associated with the exhalation inlet, configured to determine when exhaled breath is received by the exhalation inlet; and a reporter associated with the exhalation determiner, the reporter configured to provide a signal related to an exhalation duration of the exhaled breath received from the exhalation determiner to the user.

According to some embodiments of the invention, there is also provided a biofeedback device for providing biofeedback useful for helping a user control breathing, the device comprising:

a housing configured to be hand-held by the user;

an exhalation inlet for receiving exhaled breath from the mouth of the user, wherein the exhalation inlet is functionally associated with an exhalation conduit including an exhalation outlet, configured so that exhaled breath received by the exhalation inlet passes through the exhalation conduit and exits through the exhalation outlet, and a flow-restrictor functionally associated with the exhalation conduit, configured for limiting the rate of flow of the exhaled breath through the conduit;

physically associated with the housing, an exhalation determiner functionally associated with the exhalation inlet, configured to determine when exhaled breath is received by the exhalation inlet; and a reporter associated with the exhalation determiner, the reporter configured to provide a signal related to an exhalation duration of the exhaled breath received from the exhalation determiner to the user.

In some embodiments, the signal is selected from the group consisting of a visual signal (such as one or more of a symbol, a color, a light, an animation and a numerical display), an audible signal (such as one or more of a bell, a buzzer, a beep, a musical fragment, and a voice recording, and combinations thereof), a tactile signal (such as one or more of a vibration of a component, a change in temperature of a component and a change in shape of a component), and combinations thereof.

In some embodiments, the visual display is a dynamic visual display, such as a blinking visual display, an animated visual display, or a color-changing visual display, or combinations thereof.

In some embodiments, the device of the invention further comprises, physically associated with the housing, an inhalable substance outlet and a functionally-associated dispenser configured for dispensing an inhalable substance to the user through the inhalable substance outlet.

In some embodiments, the housing is configured so that when the exhalation inlet is positioned by the user for receiving exhaled breath, the inhalable substance outlet is located in proximity of the nostrils of the user.

In some embodiments, at least one of the inhalable substance outlet and the dispenser is contained within a reversibly detachable section of the housing.

In some embodiments, at least one of the inhalable substance outlet and the dispenser is contained within an integrally formed part of the housing.

In some embodiments, the device further comprises an inhalable substance reservoir functionally associated with the inhalable substance outlet, the reservoir configured to store the inhalable substance and to release the inhalable substance to the dispenser.

In some embodiments, the dispenser is a passive dispenser, comprising a reservoir configured to passively release the inhalable substance via the inhalable substance outlet.

In some embodiments, the device of the invention further comprises a cover couplable to the housing, configured to substantially prevent entry of air into the exhalation inlet when the cover is coupled to the housing.

In some embodiments, the device of the invention further comprises a cover couplable (in some embodiments, reversibly couplable) to the housing, configured to substantially prevent at least one of entry of air into the exhalation inlet, diffusion of inhalable substance out of the device prior to use, and soiling of the exhalation inlet, when the cover is coupled to the housing. In some embodiments, the device is configured so that removal of the cover activates the reporter and/or exhalation determiner. In some embodiments, the device further comprises a tether attached to at least one of the cover and the housing.

In some embodiments of the device of the invention, the exhalation inlet is functionally associated with an exhalation conduit including an exhalation outlet, configured so that exhaled breath received by the exhalation inlet passes through the exhalation conduit and exits through the exhalation outlet. In some embodiments, the exhalation conduit is contained within the housing. In some embodiments, the device further comprises a flow-restrictor functionally associated with the exhalation conduit, configured for limiting the rate of flow of exhaled breath through the conduit. In some embodiments, the exhalation determiner is configured to function as the flow-restrictor.

According to some embodiments of the invention, there is provided a biofeedback method useful for helping a user control breathing, the method comprising determining when a user is exhaling; and providing a signal related to an exhalation duration of exhaling to the user.

In some embodiments of the method of the invention, the signal comprises a comparison to a preferred exhalation duration. In some embodiments, the preferred exhalation duration is fixed. In some embodiments, the preferred exhalation duration is variable. In some embodiments, the signal further comprises a comparison to a preferred pattern of at least two exhalations.

In some embodiments of the method of the invention, the signal is selected from the group consisting of a visual signal (such as at least one of a symbol, a color, a light, an animation and a numerical display, or combinations thereof), audible signal (such as at least one of a bell, a buzzer, a beep, a musical fragment, and a voice recording), a tactile signal (such as at least one of a vibration of a component, a change in temperature of a component and a change in shape of a component), and combinations thereof.

In some embodiments, the visual display is a dynamic visual display, such as a blinking visual display, an animated visual display, a color-changing visual display.

According to an aspect of some embodiments of the invention, there is also provided a biofeedback method useful for helping a user control breathing, the method comprising:

a) providing a device for measuring exhalation duration of a user, the device having:
a variable preferred exhalation duration,
a target exhalation duration, and
a update threshold difference value;

b) for a given use-event of the device by a user, setting the preferred exhalation duration to the target exhalation duration; and c) during at least part of the given use-event of the device by the user, repeatedly determining an actual exhalation duration of the user, and if the actual exhalation duration is less than the preferred exhalation duration by at least the update threshold difference value, reducing the preferred exhalation duration, or if the actual exhalation duration is substantially equal to or greater than the preferred exhalation duration, providing a signal indicating such to the user.

In some embodiments, a signal is selected from the group consisting of a visual signal, audible signal, a tactile signal, and combinations thereof.

In some embodiments, the target exhalation duration is set through a user interface. In some embodiments, the target exhalation duration is set by the results of a previous use of the device.

In some embodiments, the method further comprises, subsequent to the determining an actual exhalation duration of the user, if the actual exhalation duration is substantially equal to the preferred exhalation duration, increasing the preferred exhalation duration.

In some embodiments, the method further comprises, subsequent to the determining an actual exhalation duration of the user, if the actual exhalation duration is greater than the preferred exhalation duration, increasing the preferred exhalation duration.

In some embodiments, the method further comprises, subsequent to the determining an actual exhalation duration of the user, if the actual exhalation duration is less than the preferred exhalation duration by less than the update threshold difference value, increasing the preferred exhalation duration.

In some embodiments, the method further comprises administering an inhalable substance to the subject, so that the subject inhales the inhalable substance between exhalations.

Unless otherwise defined, all technical and scientific terms used herein have the same meaning as commonly understood by one of ordinary skill in the art to which the invention pertains. In case of conflict, the specification, including definitions, takes precedence.

As used herein, the terms "comprising", "including", "having" and grammatical variants thereof are to be taken as specifying the stated features, integers, steps or components but do not preclude the addition of one or more additional features, integers, steps, components or groups thereof. The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed device or method.

As used herein, the indefinite articles "a" and "an" mean "at least one" or "one or more" unless the context clearly dictates otherwise.

As used herein, when a numerical value is preceded by the term "about", the term "about" is intended to indicate +/−10%.

Embodiments of methods and/or devices of the invention may involve performing or completing selected tasks manually, automatically, or a combination thereof. Some embodiments of the invention are implemented with the use of components that comprise hardware, software, firmware or combinations thereof. In some embodiments, some components are general-purpose components such as general purpose computers or oscilloscopes. In some embodiments, some components are dedicated or custom components such as circuits, integrated circuits or software.

For example, in some embodiments, some of an embodiment is implemented as a plurality of software instructions executed by a data processor, for example which is part of a general-purpose or custom computer. In some embodiments, the data processor or computer comprises volatile memory for storing instructions and/or data and/or a non-volatile storage, for example, a magnetic hard-disk and/or removable media, for storing instructions and/or data. In some embodiments, implementation includes a network connection. In some embodiments, implementation includes a user interface, generally comprising one or more of input devices (e.g., allowing input of commands and/or parameters) and output devices (e.g., allowing reporting parameters of operation and results.

BRIEF DESCRIPTION OF THE FIGURES

Some embodiments of the invention are described herein with reference to the accompanying figures. The description, together with the figures, makes apparent to a person having ordinary skill in the art how some embodiments of the invention may be practiced. The figures are for the purpose of illustrative discussion and no attempt is made to show structural details of an embodiment in more detail than is necessary for a fundamental understanding of the invention. For the sake of clarity, some objects depicted in the figures are not to scale.

In the Figures:

FIGS. 8A, 8B and 8C depict an embodiment of a device as taught herein in front view (FIGS. 8A and 8B) and perspective view (FIG. 8C);

Figure 10A:
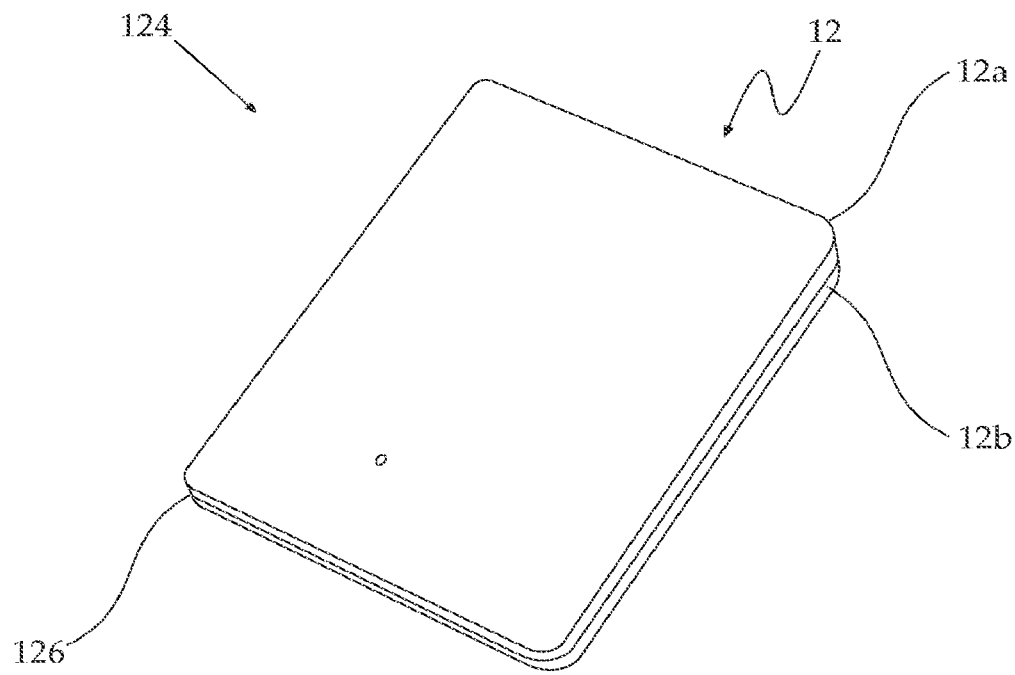
FIGS. 10A, 10B, 10C and 10D depict an embodiment of a device as taught herein in a closed configuration (FIG.
Figure 10B:
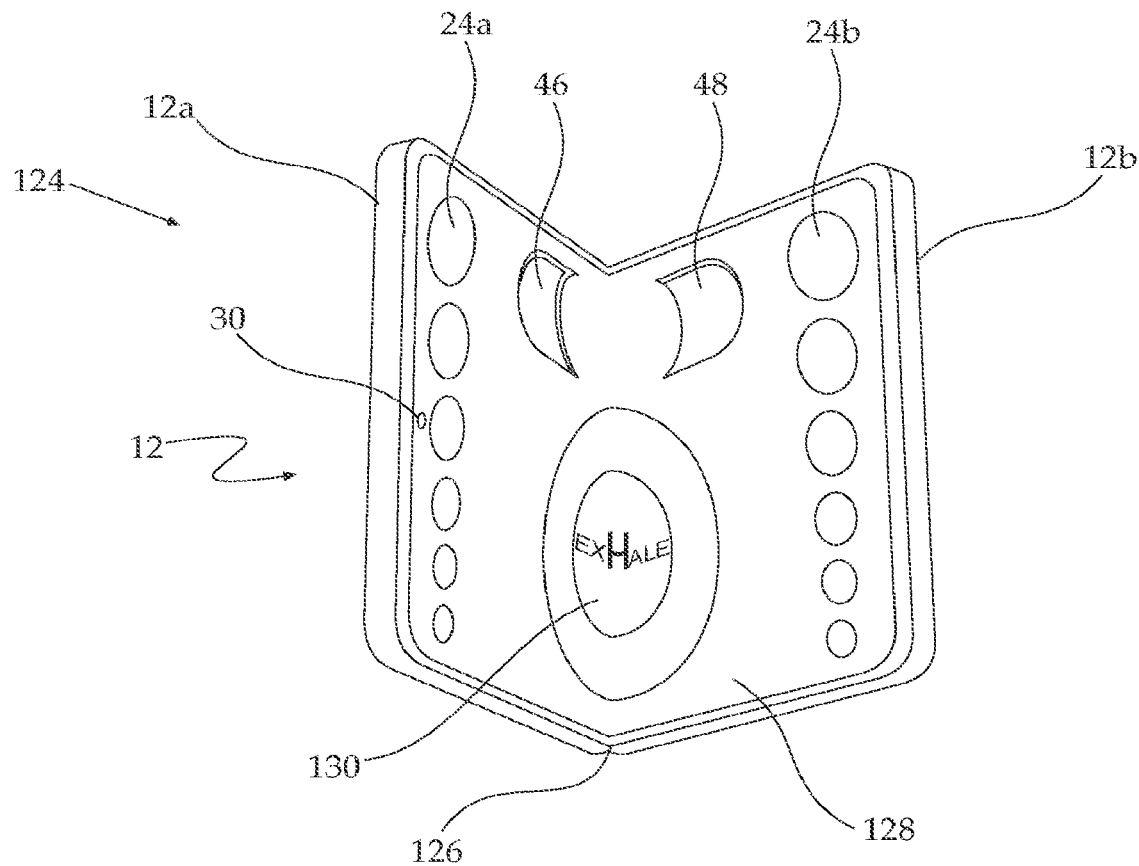
Figure 10C:
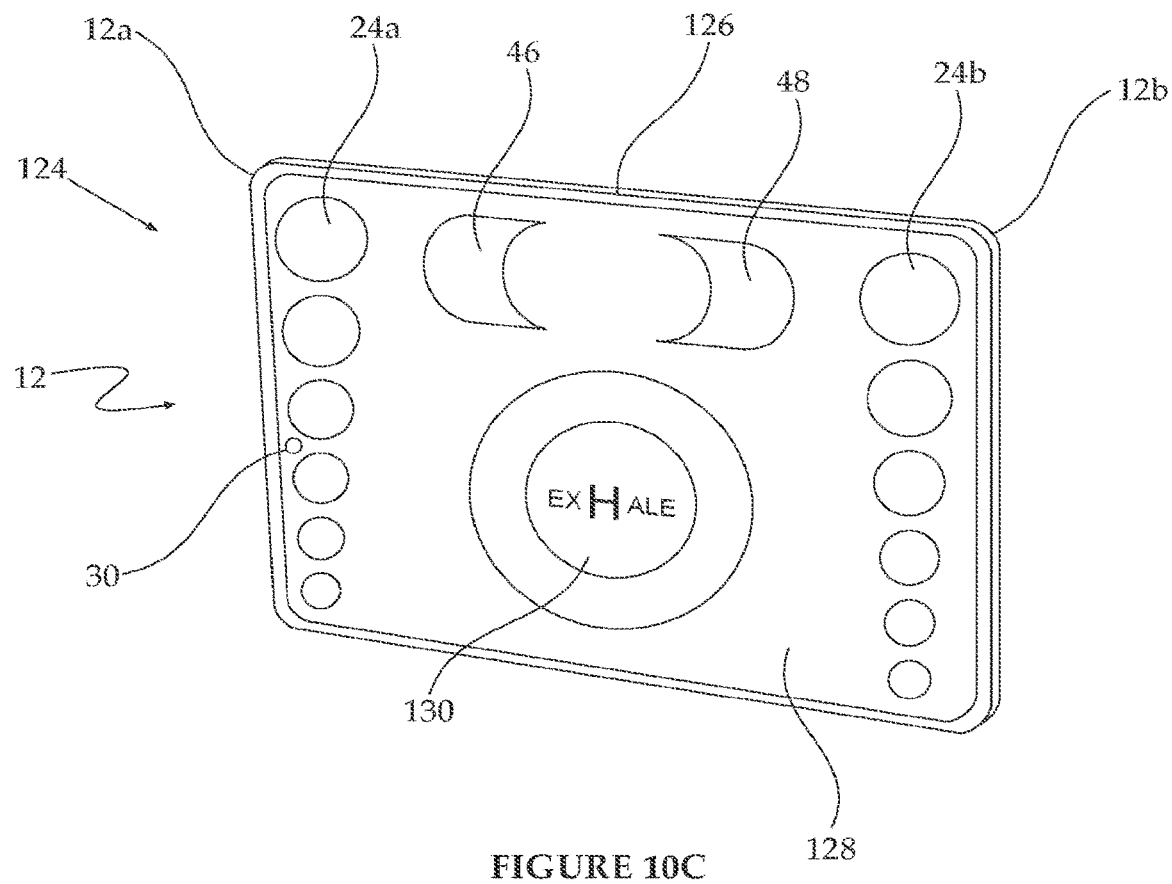
Figure 10D:
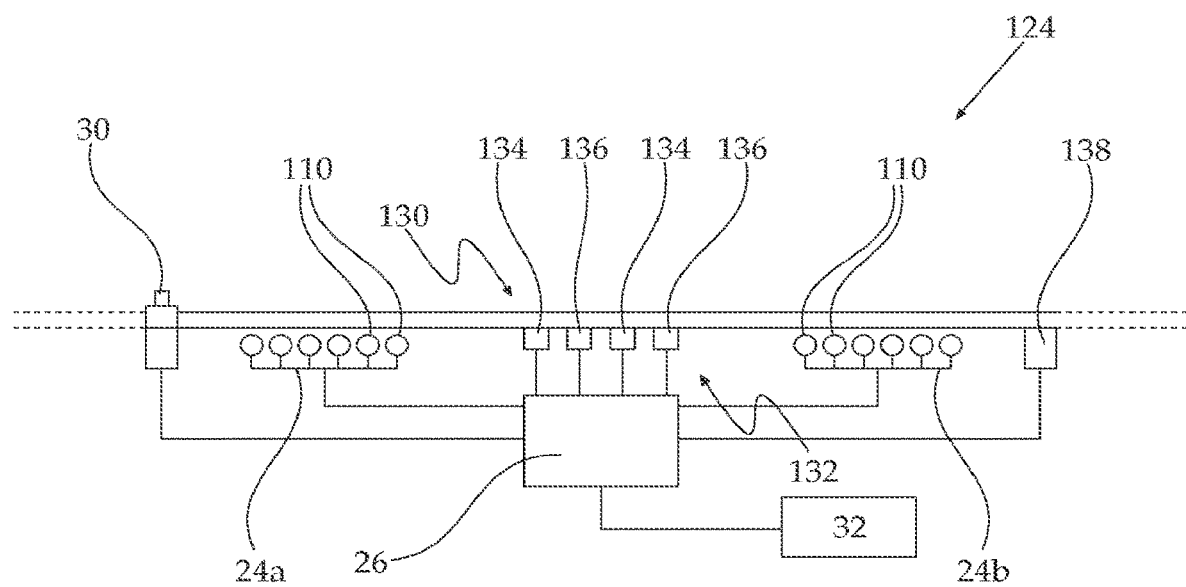

10A), in a partially-open configuration (FIG. 10B), in a fully-open configuration (FIG. 10C) and schematically (FIG. 10D).

DESCRIPTION OF SOME EMBODIMENTS OF THE INVENTION

The invention, in some embodiments, relates to the field of biofeedback, and more particularly, but not exclusively, to a device providing biofeedback for helping a user control breathing. Some embodiments of the invention relate to methods and devices that report a signal related to a preferred exhalation duration. The reported signal makes the user aware if breathing is too shallow and helps the user increase exhalation duration, in some embodiments helping to induce deep breathing.

The principles, uses and implementations of the teachings herein may be better understood with reference to the accompanying description and figures. Upon perusal of the description and figures present herein, one skilled in the art is able to implement the invention without undue effort or experimentation. In the figures, like reference numerals refer to like parts throughout.

Before explaining at least one embodiment in detail, it is to be understood that the invention is not necessarily limited in its application to the details of construction and the arrangement of the components and/or methods set forth herein. The invention is capable of other embodiments or of being practiced or carried out in various ways. The phraseology and terminology employed herein are for descriptive purpose and should not be regarded as limiting.

Method for Helping a User Control Breathing

According to an aspect of some embodiments of the invention there is provided a biofeedback method useful for helping a user control breathing, in some embodiments helping inducing deep breathing, the method comprising:
 determining when a user is exhaling; and
 providing a signal (as biofeedback) related to an exhalation duration of the exhaling to the user. In some embodiments, an additional feedback is provided that relates to the breathing pattern.

The user monitors the signal. If the exhalation duration is too short (that is to say, the breathing is too fast) the user knows to make an effort to exhale for a longer time, increasing the exhalation duration, and thereby breathing more slowly. In some embodiments, deep breathing is induced.

In some embodiments, the signal comprises a comparison to a preferred exhalation duration, making it easier for the user to know when the exhalation duration is sufficiently long. A typical preferred exhalation duration is at least about 3 seconds, typically between about 3 and about 7 seconds.

As discussed above, correct breathing is known to provide relief for various conditions. Conditions which may be treated or relieved by the method of the invention are discussed below.

Any suitable signal may be provided for the user. For example, a visual signal, an audible signal, a tactile signal or combinations thereof.

For example, in some embodiments, the signal includes or is a visual signal such as a signal selected from the group consisting of a symbol, a color, a light, a numerical display, an animation, or a combination thereof.

For example, in some embodiments the signal includes or is an audible signal such as a signal selected from the group consisting of a bell, a buzzer, a beep, a musical fragment, a voice recording, or a combination thereof.

For example, in some embodiments the signal includes or is a tactile signal such as a signal selected from the group consisting of a vibration, a change in temperature of a component, a change in the shape of a component, or a combination thereof.

Adaptive Biofeedback

In some embodiments, the method comprises adaptive biofeedback, that is to say, biofeedback that is dependent on the actual exhalation pattern of a user, for example actual determined exhalation duration. In some embodiments, adaptive biofeedback is implemented by an electrical controller by closed loop method implementation. In some embodiments, biofeedback comprises a feedback signal provided only when the exhalation time reaches at least a predetermined target threshold. In some such embodiments, no signal is provided when the user fails to reach the target threshold. In some such embodiments, a second, different signal is provided when the user fails to reach the target threshold. In some embodiments, the threshold for determining when feedback for the required exhalation time is provided is changed according to the performance of the user. In some embodiments, the threshold is set at a constant number (such as, for example, 5 seconds). In some embodiments, a constant number threshold is used only for a first-time use of the device. In some embodiments, the constant number threshold is used for subsequent uses of the device. In some embodiments, the exhalation time achieved by the user in the first exhalation is measured) and the threshold for feedback is changed accordingly. In some embodiments, if the first measured exhalation time is less than the threshold level, the threshold is decreased. In some embodiments, if the first measured exhalation time is longer than the threshold, the threshold is increased.

Some such embodiments are useful for helping a person not-necessarily suffering from an acute problem train for more effective breathing, for example, people who decide to increase lung capacity, singers, musicians, divers, and practitioners of yoga and martial arts.

Some such embodiments are useful for treating stress-related conditions especially acute stress-related conditions as discussed herein, by reducing the performance anxiety potentially arising from the need to attain a fixed preferred exhalation duration. Instead, a user gains confidence (and is calmed) by being presented with a series of attainable but increasingly difficult challenges (an increasing preferred exhalation duration).

Thus, accordingly to an aspect of some embodiments of the teachings herein, there is provided a biofeedback method useful for helping a user control breathing, the method comprising:
 a) providing a device for measuring the exhalation duration of a user, the device having: a variable preferred exhalation duration, a target exhalation duration, and a update threshold difference value;
 b) for a given use-event of the device by a user (e.g., a continuous session when the user is using the device), setting the preferred exhalation duration to the target exhalation duration; and
 c) during at least part of the given use-event of the device by the user, repeatedly determining an actual exhalation duration of the user, and
  if the actual exhalation duration is less than the preferred exhalation duration by at least the update threshold difference value, reducing the preferred exhalation duration, or if the actual exhalation duration is substantially equal to or greater than the preferred exhalation duration, providing a signal indicating such to the user, as the biofeedback.

In a descriptive non-limiting embodiment, when a user first activates such a device for a use-event, the preferred exhalation duration is set to the value of the target exhalation duration (e.g., 5 seconds).

The user exhales, and the device determines (registers) the actual exhalation duration (e.g., 1 seconds) that is less than the preferred exhalation duration (5 seconds) by more than the update threshold difference value (e.g., 0.5 seconds). Depending on the exact embodiment, the user may or may not receive biofeedback, as described above. Since the actual exhalation duration (1 second) is less than the preferred exhalation duration (5 seconds) by at least the update threshold difference value (0.5 seconds), the preferred exhalation duration is reduced, e.g., by 1 second to 4 seconds.

The user exhales a second time, and the device determines the actual exhalation duration (e.g., 1.3 seconds) that is less than the preferred exhalation duration (4 seconds) by more than the update threshold difference value (0.5 seconds). Depending on the exact embodiment, the user may or may not receive biofeedback, as described above. Since the actual exhalation duration (1.5 seconds) is less than the preferred exhalation duration (4 seconds) by at least the update threshold difference value (0.5 seconds), the preferred exhalation duration is reduced, e.g., by 1 second to 3 seconds.

The user exhales a third time, and the device determines the actual exhalation duration (e.g., 1.5 seconds) that is less than the preferred exhalation duration (3 seconds) by more than the update threshold difference value (0.5 seconds). Depending on the exact embodiment, the user may or may not receive feedback, as described above. Since the actual exhalation duration (1.5 seconds) is less than the preferred exhalation duration (3 seconds) by at least the update threshold difference value (0.5 seconds), the preferred exhalation duration is reduced, e.g., by 1 second to 2 seconds.

The user exhales a fourth time, and the device determines the exhalation duration (e.g., 1.6 seconds) that is less than the preferred exhalation duration (2 seconds) but by more update threshold difference value (0.5 seconds). Depending on the exact embodiment, the user may or may not receive feedback, as described above. Since the actual exhalation duration (1.5 seconds) is less than the preferred exhalation duration (3 seconds) by at least the update threshold difference value (0.5 seconds), the preferred exhalation duration is reduced, e.g., by 1 second to 2 seconds.

Device

The device provided to implement such an embodiment having a variable preferred exhalation duration is any suitable device, for example, devices such as described herein, that is suitably modified. Typically, a suitable device includes a digital processor and can be suitably modified without undue effort or experimentation by a person having ordinary skill in the art of programming using software and/or hardware configured to implement the teachings herein.

In some typical embodiments, the variable preferred exhalation duration, the target exhalation duration, and the update threshold difference value are implemented as variables (software or hardware) in a computer program.

Target Exhalation Duration

In some embodiments, the target exhalation duration is the ultimately-desired exhalation duration for a use-event of the device. The exact value of a target exhalation duration is embodiment-dependent.

In some embodiments, the target exhalation duration is "factory preset", that is to say, there is no simple manner to change the value thereof. In such embodiments, the value of the target exhalation duration is embodiment-dependent. For example, for embodiments suitable for treatment of stress and the like, the target exhalation duration is typically, as discussed above, at least about 3 second, typically between about 3 and about 7 seconds.

In some embodiments, the target exhalation duration is set through a user interface (e.g., entered through a user-interface of the device by the user, a parent of the user, a health care professional). Some such embodiments are exceptionally useful for training, as opposed to treatment, embodiments. In some such embodiments, there is typically no upper limit to the target exhalation duration. In some such embodiments there is an arbitrarily high upper limit (e.g., 30 seconds, 60 seconds) is integrated in the device. In some such embodiments there is a lower limit to the target exhalation duration, for example 1 second.

In some embodiments, the target exhalation duration is set by the results of a previous use of the device.

Variable Preferred Exhalation Duration

The variable preferred exhalation duration is the exhalation duration desired for a single exhalation event which purpose, in some embodiments, is constituting an attainable goal. As noted above, in some instances a following variable preferred exhalation duration is updated as a result of a previously-achieved exhalation duration.

In some embodiments, there is a minimal value below which the variable preferred exhalation duration is not set, for example, in some embodiments 1 second or 2 seconds.

Threshold Difference Value

As discussed above, the difference between an actual exhalation duration and a current preferred exhalation duration is compared to the update threshold difference value. If the actual exhalation duration is less than the preferred exhalation duration by at least the update threshold difference value, that is to say a relatively large difference, the current preferred exhalation duration is considered too long and difficult to attain, so that the preferred exhalation duration is reduced to become a more easily attainable goal. If the actual exhalation duration is less than the preferred exhalation duration by less than the update threshold difference value, that is to say a relatively small difference, the current variable preferred exhalation duration is considered an attainable goal and is therefore the preferred exhalation duration is not reduced.

The exact value of the threshold difference value is embodiment-dependent. That said, the threshold difference value in some typically embodiments, the threshold difference value is not less than 0.1 seconds and not more than 3 seconds, more typically not less than 0.2 seconds and nor more than 2 seconds.

Reducing the Preferred Exhalation Duration

The amount by which the preferred exhalation duration is reduced when needed is embodiment-dependent. In some embodiments, the amount if fixed. In some embodiments, the amount is varied, for example, as a function of the absolute value of the current value of the preferred exhalation duration and/or the value of the target exhalation duration and/or the number of exhalations and/or the purpose for which the embodiment is implemented. That said, the amount by which the preferred exhalation duration is reduced when needed is typically between about 0.1 and 1 second, more typically between 0.2 and 0.5 seconds.

Rewarding the User and Increasing the Preferred Exhalation Duration

In some embodiments, it is desirable to reward a user for an achievement with a signal as a biofeedback.

In some embodiments, certain events lead to an increase of the value of the preferred exhalation duration.

In some embodiments, the method further comprises during at least part of given use-event of the device by a user, subsequent to determining an actual exhalation duration of the user, if the actual exhalation duration is substantially equal to the preferred exhalation duration, at least one of: increasing the preferred exhalation duration and/or providing a signal thereof as a biofeedback. It is important to note that in some such embodiments the preferred exhalation duration remains unchanged.

In some embodiments, the method further comprises during at least part of given use-event of the device by a user, subsequent to determining an actual exhalation duration of the user, if the actual exhalation duration is greater the preferred exhalation duration, at least one of: increasing the preferred exhalation duration and/or providing a signal thereof as a biofeedback. It is important to note that in some such embodiments, the preferred exhalation duration remains unchanged.

In some embodiments, the method further comprises during at least part of given use-event of the device by a user, subsequent to determining an actual exhalation duration of the user, if the actual exhalation duration is less than the preferred exhalation duration by less than the update threshold difference value, at least one of: increasing the preferred exhalation duration and/or providing a signal thereof as a biofeedback. It is important to note that in some such embodiments, the preferred exhalation duration remains unchanged.

The amount by which the preferred exhalation duration is increased when needed is embodiment-dependent. In some embodiments, the amount if fixed. In some embodiments, the amount is varied, for example, as a function on the absolute value of the current value of the preferred exhalation duration and/or the value of the target exhalation duration and/or the number of exhalations and/or the purpose for which the embodiment is implemented. That said, the amount by which the preferred exhalation duration is increased when needed is typically between about 0.1 and 1 second, more typically between 0.2 and 0.5 seconds.

In some embodiments, there is no practical limit as to the upper value to which the preferred exhalation duration can be increased. In some embodiments, the upper value to which the preferred exhalation duration can be increased is the target exhalation duration. In some embodiments, some function of the last (one or few) values of the preferred exhalation durations achieved in a given use-event are used to determine a future target exhalation duration.

A provided signal is any suitable as discussed herein, and in some embodiments is a signal selected from the group consisting of a visual signal, audible signal, a tactile signal, and combinations thereof.

Inhalable Substance

In some embodiments, any of the methods further comprise administering an inhalable substance, such as an aromatherapy oil, to the subject, so that the subject inhales the inhalable substance between exhalations. Preferably, the inhalable substance is pleasant to the user or has a pharmacological effect, especially a pharmacological effect that provides relief to a condition for which the method is implemented.

In some embodiments, the inhalable substance is an active pharmaceutical ingredient.

In some embodiments, the inhalable substance is an essential oil, especially an essential oil useful for aromatherapy.

Aromatherapy is the practice of using essential oils, particularly natural essential oils extracted from aromatic plants and herbs, for the treatment of a condition or to enhance well-being. The essential oil for use in implementing the teachings herein is preferably selected according to the required use.

For example, oils or combinations thereof may be selected from any of the following: basil oil for relief of migraine, mental fatigue or nervous tension; bergamot oil as analgesic, antidepressant, antiseptic, antibiotic, anti-spasmodic, stomachic, calmative, digestive, febrifuge; black pepper oil for relief of conditions related to nicotine addiction and stress; carrot seed oil as an analgesic and anti-asthmatic, or for treatment of hypertension; chamomile oil as an analgesic, or for treatment of depression, headaches, digestive problems, eczema, irritable bowel syndrome, anxiety or fear; cedarwood oil for treatment of eczema; cinnamon oil for relief of conditions related to nicotine addiction and stress; citrodora oil for relief of conditions related to nicotine addiction and stress; citronella oil for relief of conditions related to nicotine addiction and stress; clary sage oil for relief of asthma, depression, digestive problems, exhaustion, or respiratory problems; cypress oil for treatment of asthma, relief of muscle or nerve tension; elemi oil for relief of conditions related to alcohol addiction and stress; eucalyptus oil for relief of asthma, bronchitis, headaches or muscle aches; fennel oil for relief of digestive disorders or nervous tension; frankincense oil for relief of asthma, bronchitis, nervous tension or respiratory conditions; geranium oil for relief of eczema; ginger oil for relief of bronchitis, exhaustion, or indigestion; grapefruit oil for relief of conditions related to nicotine addiction and stress, and for treatment of anxiety, depression or digestive problems; hyssop oil for relief of asthma, bronchitis or mental tension; jasmine oil for anxiety, headache, mental tension or lack of confidence; lavender oil for relief or treatment of acne, anxiety, bronchitis, eczema, headaches, insomnia, muscle aches and pains, psoriasis, or tension; lemon oil for treatment of headaches and migraine; lemongrass oil for relief of fatigue, indigestion, muscle aches and pains, appetite loss, and stress; lime oil for relief of conditions related to nicotine addiction; mandarin oil for stress relief, marjoram oil for relief of arthritis, bronchitis, digestive problems, insomnia, muscle aches and pains; lemon balm oil for stress or menstrual symptoms; marjoram oil for relief of conditions related to nicotine addiction and stress; nutmeg oil for relief of conditions related to nicotine addiction and stress; palmarosa oil for relief of conditions related to nicotine addiction and stress; neroli oil for relief of depression, digestive problems, headaches, insomnia, irritable bowel syndrome, nervous tension, panic attacks or stress; orange oil for relief of anxiety, depression, digestive problems, insomnia, muscle aches and pains, nervous tension, respiratory conditions or stress; patchouli oil for relief of anxiety, depression or eczema; peppermint oil for relief of asthma, bronchitis, headaches, indigestion, migraine, muscle and joint pain; petitgrain oil for relief of anxiety, digestive problems, exhaustion, insomnia, respiratory problems or stress; pine oil for treatment of respiratory disorders; rose oil for relief of depression, headache, insomnia or stress; rosemary oil for relief of conditions related to nicotine addiction, to boost memory recall and concentration, for mild depression and for fatigue; sandalwood oil for relief of anxiety, bronchitis, fatigue, nervous tension, eczema, nicotine addiction or stress; spearmint oil for relief of conditions related to nicotine addiction and stress; thyme oil for relief of conditions related to nicotine addiction and for relief of depression, fatigue, or stress; vanilla oil for treatment of sexual dysfunction, depression, insomnia, or stress; vetiver oil for relief of conditions related to nicotine addiction and for relief of exhaustion, insomnia, nervousness, or stress; ylang ylang oil for relief of anxiety, high blood pressure, intestinal problems, sexual dysfunction or stress; and wintergreen oil for relief of headaches, hypertension, eczema, psoriasis or ulcers.

The methods described herein can be implemented using any suitable device. That said, in some embodiments it is preferred to implement the method using a device as described herein.

Device for Helping a User Control Breathing

According to an aspect of some embodiments of the invention there is provided a biofeedback device for providing biofeedback useful for helping a user control breathing, in some embodiments helping inducing deep breathing, the device comprising:

a housing configured to be hand-held by the user;

an exhalation inlet for receiving exhaled breath of the user;

physically associated with the housing, an exhalation determiner functionally associated with the exhalation inlet, configured to determine when exhaled breath is received by the exhalation inlet; and a reporter associated with the exhalation determiner, the reporter configured to provide a signal related to an exhalation duration of the exhaled breath received from the exhalation determiner to the user.

In some embodiments, the reporter is further configured to provide a signal related to an exhalation pattern.

In some embodiments, a device is a small, discrete, portable device which can be carried by a user, for example in a bag or pocket, to use as needed, for example in stress-related situations, to prevent the onset or reduce the severity of conditions caused or exacerbated by stress. In some embodiments, the device may be used on a regular basis, such as according to a defined schedule, for treatment or relief of stress-induced disorders. In some embodiments, the device may be used on a regular basis, such as according to a defined schedule, for treatment or relief of disorders that are not related to stress. In some embodiments, the device may be used as-needed on an ad hoc basis for treatment or relief of a disorder, including stress-related disorders and disorders that are not related to stress. In some embodiments, the device may be used under non-stress conditions as a training device to help a user practice deep breathing techniques e.g. for yoga exercises, martial arts or voice training.

In some embodiments, the housing of a device is as small and lightweight. The housing is preferably formed from any suitable non-allergenic, non-corroding material of sufficient strength to resist deformation or damage when carried, for example, in a handbag or pocket, and to provide protection to the assemblies and components contained therein.

Suitable materials for construction of the housing include materials known in the field of portable telephony such as rigid polymers, for example, polycarbonates, copolyesters, acrylics, ABS, nylon, polystyrene, polypropylene, polyethylene, polysulfone, and polyimide as well as light-weight metals such as magnesium. Preferably, the housing is sufficiently small to enable the device to be concealed within the hand of the user during use (e.g., in some embodiments not more than about 200 g and even not more than 100 g; having dimensions typically similar or smaller than of a box of cigarettes, e.g., in some embodiments having a greatest dimension not greater than about 150 mm, and even not greater than about 120 mm). In some embodiments, the housing has a height (i.e., when properly held for use, in the mouth-to-nose direction) in the range of about 55 to 80 mm. In some embodiments, the housing has a width (i.e., when properly held for use in the ear-to-ear direction) in the range of from about 30 to about 120 mm. In some embodiments, the width is in the range of from about 35 to about 50 mm. In some embodiments, the housing has a length of from about 10 to about 75 mm.

In some embodiments, the outside of the housing is provided in a color considered to exert a calming effect, such as, for example, pink, blue, white, purple, gray or green. In some embodiments, the color of the housing is selected to be similar to the skin color of the user so that the device is unobtrusive during use.

A housing of any suitable shape may be used in implementing the teachings herein.

In some embodiments, the signal comprises a comparison to a preferred exhalation duration, making it easier for the user to know when the exhalation duration is sufficiently long. In such embodiments, a reporter typically includes a timer, clock or similar component. In some embodiments, a reporter includes a controller. A typical preferred exhalation duration is at least about 3 seconds, typically between about 3 and about 7 seconds.

The reporter is configured to provide any suitable signal. For example, a visual signal, an audible signal, a tactile signal or combinations thereof.

For example, in some embodiments, the signal includes or is a visual signal. Any suitable visual signal may be used. Non-limiting examples of visual signals include an animation, a symbol, such as a tick, a check, a heart, or a 'smiley', 'thumbs up' or 'kiss' icon which is displayed only when the exhalation duration is within the desired range. In some embodiments, a light of a specific color is displayed when the exhalation duration is within the desired range, or a change of color is displayed during exhalation. In some embodiments, the visual signal comprises a numerical display of the exhalation duration or of time elapsed during exhalation. In some embodiments, a series of different colored lights are sequentially activated to indicate the duration of exhalation. In some embodiments, the visual signal may be preselected by the user from a number of options.

In some such embodiments, a visual signal is an image (e.g., a photograph) that the user enjoys seeing (e.g., a photograph of a beloved animal). For example the image is at least partially, preferably completely, obscured when exhalation begins and is entirely unobscured and apparent if the exhalation duration is sufficiently long.

In some embodiments, the device further comprises a screen for display of the visual signal. Preferably, the location of such a screen is selected such that the visual signal is visible to the viewer during use of the device without requiring the device to be removed from proximity with the mouth. For example, in some embodiments of devices having a tube-shaped housing, the screen is located on a surface of the housing facing the user's face when the tube is inserted into the mouth. In some embodiments, the device housing comprises a raised section on which a display screen is located.

For example, in some embodiments the signal includes or is an audible signal. Any suitable audible signal may be used. Non-limiting examples include a bell, a buzzer, a beep, a musical fragment, or a voice recording (for example, stating the value of the measured exhalation duration). In some embodiments, the audible signal is sounded only when the exhalation duration is within the desired range. In some embodiments, the same or different audible signals are sounded intermittently, for example, each second that the user exhales. In some embodiments, the audible signal may be preselected by the user from a number of options. In some embodiments, the audible signal is recorded and/or stored by a user in a device.

In some embodiments, a visual and/or audible signal are defined by the user, for example, an audible signal chosen, acquired, generated, recorded and/or composed by the user, or a visual signal chosen, acquired, generated, recorded and/or captured by the user. In some such embodiments, a device used in implementing the method is configured to allow uploading and storage of such visual and/or audible signal, for example, includes a USB or Bluetooth® port functionally associated with a device memory (e.g., flash memory), allowing upload and storage of visual and/or audible signals.

For example, in some embodiments the signal includes or is a tactile signal such as a vibration, a change in temperature of a component of the device, for example of at least part of the casing, or a change in the shape of a component of the device, for example a progressively protruding knob or figure, for example, a figurine.

According to some embodiments, the signal may be communicated to a component or device remote from the housing. For example, a visual signal may be displayed on spectacles adapted for wired or wireless communication with the device; on a remote screen; on a mobile phone or the like. An audible or tactile signal may be communicated to a mobile phone, a wireless earpiece, a waistband, a bracelet, a ring or a hand-held ball.

In some embodiments, the device further comprises, physically associated with the housing, an inhalable substance outlet and a functionally-associated dispenser configured for dispensing an inhalable substance to the user through the inhalable substance outlet.

In some embodiments, the dispenser is a passive dispenser, such as a reservoir containing an inhalable substance, such that the inhalable substance is passively released from the reservoir and wafts from the inhalable substance outlet. In some embodiments, the dispenser is an active dispenser including components that increase the amount of inhalable substance dispensed when activated, for example, by the flow of air and/or by heating of a component (e.g., a vaporizer) and/or by vibrating a component (e.g., a piezoelectric nebulizer).

In some embodiments, the inhalable substance outlet and the dispenser are contained within a reversibly detachable section of the housing. In some embodiments, the inhalable substance outlet and the dispenser are contained within a section of the housing that is permanently affixed or integrally-formed with other parts of the housing.

The housing of a device as described herein may be of any suitable and useful shape, including straight, curved, C-shaped, J-shaped, K-Shaped, L-shaped, U-shaped and V-shaped In some embodiments, the housing is configured to change in shape.

In some embodiments, the housing is configured so that when the exhalation inlet is positioned by the user for receiving the exhaled breath, the inhalable substance outlet is located in proximity of the nostrils of the nose of the user.

In some such embodiments, the device comprises a substantially 'U' shaped housing, having a rounded or squared (flat) base portion, such that the end of a first arm of the 'U' comprises the exhalation inlet and the end of a second arm of the 'U' comprises the inhalable substance outlet, with the dispenser contained within the body of the 'U'. The proximal ends of the two arms of the 'U' are preferably spaced apart such that inhalable substance outlet is proximal to the nose of the user when the exhalation inlet is positioned in or adjacent to the mouth of the user. In some such embodiments, the distance between the proximal ends is adjustable by the user. In some such embodiments, the arm comprising the inhalable substance outlet is preferably slightly shorter than the arm comprising the exhalation inlet, in order to accommodate the nose of the user.

In some embodiments, the device further comprises an inhalable substance reservoir functionally associated with the inhalable substance dispenser, the reservoir configured to store the inhalable substance and to release the inhalable substance to the dispenser.

The reservoir is constructed of any suitable material and may have any suitable shape. Typical but non-limiting examples of reservoirs suitable for storing and dispensing essential oils include a sealed reservoir containing the oil, wherein the seal is broken prior to use; a diffuser, such as a steam diffuser; a solid material such as a pad or cloth or plastic article impregnated with the oil; a slow release polymeric film comprising the oil (such as described in U.S. Pat. No. 3,994,439); a composition comprising a water-soluble gel which releases the essential oil with gradual evaporation of water; a slow-release composition comprising an ethylene-vinyl acetate polymer, such as disclosed in U.S. Pat. No. 4,492,644; or any other suitable reservoir. In some embodiments, the essential oil is contained in a solid material and exposure to air (for example, exhaled air passing through the device or air entering the device upon opening thereof) causes release of the inhalable substance.

In some embodiments, the inhalable substance is an active pharmaceutical ingredient.

In some embodiments, the inhalable substance is an essential oil, especially an essential oil useful for aromatherapy. Typical essential oils include allspice oil; ambrette oil; anise oil; basil oil; bergamot oil; black pepper oil; borneol oil; cajeput oil; calamintha oil; camphor white oil; carrot seed oil; cedarwood oil; chamomile oil; cinnamon oil; citrodora oil; citronella oil; clary sage oil; coriander oil; cypress oil; elemi oil; eucalyptus oil; fennel oil; frankincense oil; galbenum oil; geranium oil; ginger oil; grapefruit oil; helichrysum oil; hemlock oil; hyssop oil; jasmine oil; lavender oil; lavendin oil; lemon oil; lemon balm oil; lemongrass oil; lime oil; mandarin oil; marjoram oil; mastic oil; mint oil; myrrh oil; niaouli oil; neroli oil; nutmeg oil; orange oil; palmarosa oil; patchouli oil; peppermint oil; petitgrain oil; pine oil; rose oil; rosemary oil; sage oil; sandalwood oil; silver fir oil; spearmint oil; spruce oil; star anise oil; thyme oil; turmeric oil; turpentine oil; vanilla oil; vetiver oil; wintergreen oil; and ylang ylang oil; or combinations thereof.

In some embodiments, the inhalable substance is selected as having an effect for the relief or treatment of a stress-related condition, for example, in some embodiments a stress-related condition is selected from the group consisting of abdominal pain, acne, addiction, agitation, allergy, anxiety, appetite loss, arthritis, asthma, attention deficit syndrome, blepharospasm, bowel disorders, bronchitis, cardiovascular disorders, chronic fatigue syndrome, chronic pain, dermatitis, cold extremities, digestive disorders, dysmenorrhea, eczema, endocrine disorders, fatigue, headaches, hyperhidrosis, hypertension, fear of flying, insomnia, irritable bowel syndrome, labor pain, mental fatigue, mental stress, migraine, muscle aches, neck pain, nervous tension, panic attacks, phobia, poor concentration, post traumatic disorders, psoriasis, psychosomatic conditions, rashes, respiratory disorders, sexual dysfunction, sleep disorders, sinus congestion, test anxiety, and ulcers.

In some embodiments, an inhalable substance for treatment of a stress-related condition is selected from the group consisting of basil oil, bergamot oil, black pepper, cedarwood oil, chamomile oil, cinnamon oil, citrodora oil, clary sage oil, cypress oil, elemi oil, eucalyptus oil, fennel oil, frankincense oil, geranium oil, ginger oil, grapefruit oil, hyssop oil, jasmine oil, lavender oil, lemon oil, lemon balm oil, lemongrass oil, lime oil, mandarin oil, marjoram oil, neroli oil, nutmeg oil, orange oil; palmarosa oil; patchouli oil, peppermint oil; petitgrain oil, rose oil; rosemary oil, sandalwood oil, spearmint oil; thyme oil; vanilla oil; vetiver oil; wintergreen oil; and ylang ylang oil; and combinations thereof.

In some embodiments, the stress related condition is a psychosomatic disorder. In some embodiments, the psychosomatic disorder is selected from the group consisting of abdominal pain, allergy, asthma, blepharospasm, dysmenorrhea, essential hypertension, lower back pain, migraine and tension headaches, hyperhidrosis, irritable bowel syndrome, myofascial pain, pain, psychogenic emesis, Raynaud's disease, tinnitus, writer's cramp, and performance anxiety.

In some embodiments, an inhalable substance for treatment of a psychosomatic disorder is selected from the group consisting of basil oil; carrot seed oil; chamomile oil; cedarwood oil; clary sage oil; cypress oil; eucalyptus oil; fennel oil; frankincense oil; geranium oil; ginger oil; grapefruit oil; hyssop oil; jasmine oil; lavender oil; lemon oil; lemongrass oil; lime oil; marjoram oil; lemon balm oil; neroli oil; orange oil; patchouli oil; peppermint oil; petitgrain oil; pine oil; rose oil; rosemary oil; sandalwood oil; thyme oil; vetiver oil; ylang ylang oil; wintergreen oil; and vanilla oil.

In some embodiments, the method or device is useful in rehabilitation therapy. In some embodiments, the rehabilitation therapy comprises rehabilitation of a subject suffering from a condition selected from the group consisting of causalgia, cerebral palsy, esophageal motility disorders, dysphagia, Guillain barre syndrome, hemiplegia, multiple sclerosis, neuromuscular reeducation, orthopedic recovery enhancement, paretic muscles, Parkinson's disease, post-cva rehabilitation, reduction of spasticity and hypertonicity, respiratory disorders, spinal cord injuries, stress management, stroke, tendon transfer, tic, and torticollis.

In some embodiments, a method or device useful in rehabilitation therapy comprises an inhalable substance selected from the group consisting of allspice oil, ambrette oil, aniseed oil, basil oil (including French basil oil), bay oil (including West Indian bay oil), bergamot oil, borneol oil, black pepper, cajeput oil, calamintha oil, camphor-white oil, chamomile oil, cedarwood oil, cinnamon oil, citrodora oil, clary sage oil, coriander oil, cypress oil, elemi oil, eucalyptus oil (including blue gum and peppermint), fennel oil, frankincense oil, galbanum oil, geranium oil, ginger oil, grapefruit oil, helichrysum oil, hemlock oil, hyssop oil, jasmine oil, lavender oil (including spike and true lavender oil), lavendin oil, lemon oil, lemongrass oil, lime oil, mandarin oil, marjoram oil, lemon balm oil, marjoram oil, mastic oil, mint oil (including peppermint and spearmint oil), nutmeg oil, palmarosa oil; neroli oil, niaouli oil, nutmeg oil, orange oil; patchouli oil, peppermint oil; petitgrain oil, pine oil (including longleaf and Scotch pine oil); rose oil; rosemary oil, sage oil (including clary and Spanish sage oil), sandalwood oil, silver fir oil; spearmint oil; spruce oil; star anise oil; thyme oil; turmeric oil; turpentine oil; vetiver oil; ylang ylang oil; wintergreen oil; and vanilla oil; or combinations thereof.

In some embodiments, a method or device useful in muscle pain and rehabilitation comprises an inhalable substance selected from the group consisting of allspice, ambrette, star anise, aniseed, French basil, west Indian bay, borneol, cajeput, calamintha, camphor-white, chamomile, coriander, cypress, eucalyptus (blue gum and peppermint), Silver fir, galbanum, ginger, grapefruit, helichrysum, jasmine, lavandin, lavender (spike and true), lemongrass, sweet marjoram, mastic, mint (peppermint and spearmint), niaouli, nutmeg, blackpepper, pine (longleaf and Scotch), rosemary, sage (clary and Spanish), hemlock spruce, thyme, turmeric, turpentine, and vetiver.

In some embodiments, the method or device is useful in the treatment of a condition which is at least partially unrelated to stress, the condition selected from the group consisting of acne, anger states, arthritis, attention deficit disorder, backache/neck pain, balance disorders, behavioral control (including addictions, such as alcohol addiction, drug addiction, nicotine addiction), bronchitis, bruxism, cardiac arrhythmia, cardiovascular disorders, carpal tunnel syndrome, chronic fatigue syndrome, chronic pain, concentration disorders, diabetes, dermatitis, cold extremities, digestive disorders, dysmenorrhea, eczema, endocrine disorders, epilepsy, fatigue, headaches, hyperhidrosis, hypertension, insomnia, impotence, incontinence, irritable bowel syndrome, labor pain, learning disabilities, mental fatigue, migraine, muscle aches, neck pain, poor concentration, postural dysfunction, rashes, respiratory disorders, sexual dysfunction, sleep disorders, sinus congestion, and ulcers.

In some embodiments, a method or device for treatment of a condition at least partially unrelated to stress comprises an inhalable substance selected from the group consisting of basil oil; bergamot oil; black pepper oil; carrot seed oil; cedarwood oil; chamomile oil; cinnamon oil; citrodora oil; citronella oil; clary sage oil; cypress oil; elemi oil; eucalyptus oil; fennel oil; frankincense oil; geranium oil; ginger oil; grapefruit oil; hyssop oil; jasmine oil; lavender oil; lemon oil; lemon balm oil; lemongrass oil; lime oil; marjoram oil; neroli oil; nutmeg oil; orange oil; palmarosa oil; patchouli oil; peppermint oil; petitgrain oil; pine oil; rose oil; rosemary oil; sandalwood oil; spearmint oil; thyme oil; vetiver oil; ylang ylang oil; wintergreen oil; and vanilla oil; and combinations thereof.

In some embodiments, the method or device of the invention is useful in the treatment of addiction, such as substance addiction (for example, at least one of alcohol addiction, drug addiction, and smoking or nicotine addiction).

In some embodiments, a method or device for treatment of a condition comprising smoking or nicotine addiction comprises an inhalable substance selected from the group consisting of anise, bergamot, black pepper, cedarwood, chamomile, cinnamon, citrodora, citronella, clary sage, eucalyptus, fennel, frankincense, geranium, grapefruit, lavender, lemon, lemongrass, lime, marjoram, nutmeg, orange, palmarosa, peppermint, pine, rosemary, sandalwood, spearmint, thyme, vetiver, and ylang ylang, or combinations thereof.

In some embodiments, a method or device for treatment of a condition comprising alcohol addiction comprises an inhalable substance for the relief of difficulties associated with withdrawing from alcohol addiction, wherein the inhalable substance is selected from the group consisting of fennel oil; clary sage oil; bergamot oil; elemi oil; frankincense oil; lavender oil; neroli oil; thyme oil; and ylang ylang oil, or combinations thereof.

In some embodiments, the method or device is useful in the treatment of difficulties associated with dieting.

In some embodiments, a method or device useful in the treatment of difficulties associated with dieting comprises an inhalable substance for relief of difficulties associated with dieting, wherein the inhalable substance comprises an essential oil selected from the group consisting of orange oil; lemon oil; grapefruit oil; rosemary oil; peppermint oil; ginger oil; and basil oil, or combinations thereof.

In some embodiments, the method or device of the invention is useful in performance and lifestyle applications, such as, for example, sports applications (improvement of performance in a sport), stress management, and voice-coaching.

In some embodiments, a method or device useful in performance and lifestyle applications comprises an inhalable substance selected from the group consisting of basil oil, bergamot oil, black pepper, chamomile oil, cedarwood oil, cinnamon oil, citrodora oil, clary sage oil, cypress oil, elemi oil, eucalyptus oil, fennel oil, frankincense oil, geranium oil, ginger oil, grapefruit oil, hyssop oil, jasmine oil, lavender oil, lemon oil, lemongrass oil, lime oil, mandarin oil, marjoram oil; lemon balm oil; marjoram oil, nutmeg oil; palmarosa oil; neroli oil, orange oil; patchouli oil, peppermint oil; petitgrain oil, rose oil; rosemary oil, sandalwood oil, spearmint oil; thyme oil; vetiver oil; ylang ylang oil; wintergreen oil; and vanilla oil.

In some embodiments wherein the performance and lifestyle application comprises voice-coaching, the inhalable substance is selected from the group consisting of Tolu balsam, benzoin, caraway, cubeb, lemon, eucalyptus, frankincense, jasmine, lavandin, lavender, myrrh, sage, sandalwood, and thyme.

In some embodiments, the device further comprises a cover couplable to the housing, configured to substantially prevent entry of air into the exhalation inlet and/or to cover the inhalable substance outlet and/or to conceal the nature of the device when the cover is coupled to the housing and/or to maintain the various inlets and outlets clean and/or to prevent evaporation of an essential oil. In some embodiments, the cover is reversibly couplable to the housing. In some embodiments the cover comprises a cap configured to fit over the mouthpiece or over the inhalable substance outlet. In some embodiments, the device is configured so that removal of the cover activates the reporter and/or the exhalation determiner. In some embodiments, the device further comprises a tether (e.g., key-chain) attached to at least one of the cover and the housing, allowing the device to be easily connected (tied) to something, for example, a bag. In some embodiments, the device comprises a cover connector for maintaining association of the cover and the housing, preventing the cover from being lost when the device is in use. The connector may comprise, for example, a plastic or metal wire, or a thin chain.

In some embodiments, a device is devoid of a cover. In some embodiments, a device is devoid of a cover and includes a tether. In some embodiments, a device is devoid of both a cover and a tether.

In some embodiments, the exhalation inlet is functionally associated with an exhalation conduit including an exhalation outlet, and the device is configured so that exhaled breath received by the exhalation inlet passes through the exhalation conduit and exits (to the surroundings) through the exhalation outlet. In some embodiments, the exhalation conduit is contained within the housing.

In some embodiments, the device further comprises a flow-restrictor functionally associated with the exhalation conduit configured for limiting the rate of flow of the exhaled breath through the conduit. Specifically, in some embodiments a flow-restrictor allows a certain exhalation flow rate to be exhaled substantially unimpeded, but higher flow rates are impeded. Such a flow-restrictor allows free flow of breath through the exhalation conduit at a relatively low (thus desirable) rate, but generates resistance to a too forceful flow of breath through the exhalation conduit. The generated resistance acts as a reminder to the user to slow down the rate of exhalation. A flow-restrictor is typically defined by dimensions and/or shape of some or all of the exhalation conduit, for example, width, length and shape (curved, angled) of the exhalation conduit. In some embodiments, a flow-restrictor, is defined by the cross-sectional area of some or all of the exhalation conduit, for example being between 0.13 cm$^2$ (equivalent to a circle with a 0.2 cm radius) and 3.8 cm$^2$ (equivalent to a circle with a 1.1 cm radius). In some embodiments, the exhalation determiner is configured to function as the flow-restrictor.

In some embodiments, the device is devoid of a flow-restrictor and exhalation, even at high flow rates and/or pressure, does not encounter substantial resistance.

In some embodiments, the device further comprises a one-way valve functionally associated with the exhalation conduit, configured for allowing passage of exhaled breath from the exhalation inlet through the exhalation conduit and out through the exhalation outlet but for preventing inhalation of air from the exhalation outlet, through the exhalation conduit and out through exhalation inlet. If a user mistakenly tries to inhale through the mouth and not through the nose, not in keeping with the desired breathing pattern, the one-way valve prevents air from being inhaled through the mouth. The user senses that inhalation through the mouth is not possible and instead resumes inhaling through the nose. It is important to note that the one-way valve acts as a reminder to the user and is not dangerous. If, for any reason, the user does not want to, or cannot, inhale through the nose, the user can simply release the mouthpiece and inhale through the mouth. Furthermore, in embodiments comprising an inhalable substance, the valve prevents the user from swallowing the substance.

In some embodiments, the device is devoid of a one-way valve and a user can inhale air through the exhalation inlet, drawing air into the mouth.

In some embodiments, a device includes both a one-way valve as described above and a flow-restrictor as described above. In some such embodiments, an exhalation determiner is configured to function as the one-way valve. In some embodiments, a device includes separate components, some function as a one-way valve and some as a flow-restrictor.

In some embodiments, a device includes a one-way valve as described above but is devoid of a flow-restrictor as described above.

In some embodiments, a device is devoid of a one-way valve as described above but includes a flow-restrictor as described above.

In some embodiments, a device is devoid of both a one-way valve as described above and a flow-restrictor as described above.

In some embodiments, the device includes an 'on/off' button or switch for activation/deactivation of the device. In some embodiments, the button is pressed or the switch position moved to the 'on' position manually by the user in order to activate the device. In some embodiments, the device is provided with a protruding button, wherein the device is inactive when the switch is depressed, and activated when the button is released. In some such embodiments, the device is inactive when a couplable cover as described above is coupled with the housing, for example depresses a button, and the device is activated automatically upon removal of the cover such that the button is released. In some embodiments comprising a dispenser for an inhalable substance, activation of the dispenser may be effected independently from activation of the assembly for measurement of exhalation duration. Alternatively, the dispenser may be activated manually or automatically following completion of measurement of exhalation duration, e.g. after a preset number of exhalations are made, or preset number of exhalations within the desired range are made, or after a preset time. According to some embodiments, a device as described herein is battery-operated. In some embodiments, electrical power is provided by other components (in addition to or instead of a battery), for example, one or more capacitors to store electricity, cells to convert light to electricity, fuel-cells and motion-powered generators to generate electricity from motion, e.g., shaking, rotation.

In some embodiments, upon activation of the device a signal is given to a user to commence exhalation after a predetermined time period. The signal to commence exhalation may be a visual and/or an audible and/or tactile signal, and may be the same as or different to the signal related to exhalation duration described above. For example, both signals may be visual/audible/tactile signals, or one of the signals may be one of visual/audible/tactile and the other signal may be another of visual/audible/tactile. In embodiments comprising a screen for display of a signal related to exhalation duration, a visual signal to commence exhalation may be displayed upon the same screen, or upon a second screen, and may comprise a different or the same visual signal as that related to exhalation duration.

In some embodiments, for use a user activates the device. In embodiments wherein the device is activated by removal of the cover, the cover is removed to activate the device. In embodiments wherein the device is activated by a button or switch, the user presses or moves the button or switch. In some embodiments comprising a cover and an activation switch, the user first removes the cover, then activates the device by use of the switch. In some embodiments comprising a cover and an activation switch, the user first activates the switch and then removes the cover. In some embodiments, a device requires no particular user-action to be activated.

The user then places the exhalation inlet in proximity of the mouth (in some embodiments at least partially held in the mouth, but in some embodiments not contacting any part of the mouth) and exhales thereinto. In some embodiments a signal is provided to commence exhalation. In some such embodiments, the user first waits for the signal before commencing exhalation. In some embodiments, the user may choose to commence exhalation prior to receiving the signal. In some embodiments no signal is provided and the user simply commences exhalation when desired.

For a period of time, the user continues breathing with the exhalation inlet in proximity of the mouth, exhaling through the mouth and into the exhalation inlet.

At any given exhalation, the user tries to exhale until the reporter provides a signal indicating that the exhalation duration is sufficient. If this is achieved, the user continues breathing with substantially the same exhalation duration, for example until a required degree of relaxation is achieved, assured that breathing is correct and, in some embodiments, inhaling an inhalable substance.

If at a given exhalation the reporter does not provide a signal indicating that the exhalation duration is sufficient, the user knows to exhale for a longer duration until a sufficient exhalation duration is achieved and, in some embodiments, inhaling an inhalable substance.

In some embodiments, the device measures a more complex breathing pattern, such as, for example, a breathing pattern that includes at least two breathing cycles (inhalation/exhalation) with a variable exhalation duration or time between two exhalations. In some embodiments the user is able to select or input a desired complex breathing pattern and the device then provides relevant feedback to actualize the desired complex breathing pattern. For example, in some embodiments, a device provides a first feedback when the user achieves a required exhalation duration and the device provides a second feedback when the user completes the desired complex breathing pattern (e.g., 5 cycles of 2 seconds exhalation duration with time difference of less than 1 second between subsequent exhalations as preferred during childbirth). Some such embodiments are exceptionally useful, for example, for use during labor: a suitably configured device can be used by a woman in labor to assist in maintaining a proper breathing pattern.

Exhalation duration can be measured using any suitable method or device, for example, by determining the presence of flow through an exhalation conduit.

In some embodiments, a device comprises at least one pressure sensor (e.g., piezoelectric pressure sensor, metal/ceramic/silicone diaphragm pressure sensor) configured to measure exhalation duration. For example, in some such embodiments the device is configured so that a user exhales directly at a pressure sensor, and the pressure applied by the exhalation is an indication of exhalation. In some embodiments, a device comprises at least one temperature sensor (e.g., thermistor, for example an MCP9700 or MCP 9701 series low-power linear active thermistor integrated circuit available from Microchip Technology Inc, Chandler, Arizona, USA) configured to measure exhalation duration. For example, in some such embodiments the device is configured so that a user exhales directly at a temperature sensor, and the difference between the temperature of the exhaled breath and ambient temperature is taken as an indication of exhalation. In some such embodiments, the device includes at least one temperature sensor to measure ambient temperature.

When desired, the user stops using the device. If applicable, the device is deactivated, for example, by replacing the cover or by pressing a button or changing the position of a switch. If applicable and/or desired, the device is cleaned, especially the exhalation inlet. In some embodiments, the device is discarded.

Conditions Treatable by Controlled Breathing

In some embodiments, the method or device of the invention is useful for the relief or treatment of a condition responsive to controlled breathing.

In some embodiments, the condition is stress-related condition, for example, in some embodiments a stress-related condition is selected from the group consisting of abdominal pain, acne, addiction, agitation, allergy, anxiety, appetite loss, arthritis, asthma, attention deficit syndrome, blepharospasm, bowel disorders, bronchitis, cardiovascular disorders, chronic fatigue syndrome, chronic pain, dermatitis, cold extremities, digestive disorders, dysmenorrhea, eczema, endocrine disorders, fatigue, headaches, hyperhidrosis, hypertension, fear of flying, insomnia, irritable bowel syndrome, labor pain, mental fatigue, mental stress, migraine, muscle aches, neck pain, nervous tension, panic attacks, phobia, poor concentration, post traumatic disorders, psoriasis, psychosomatic conditions, rashes, respiratory disorders, sexual dysfunction, sleep disorders, sinus congestion, test anxiety, and ulcers.

In some embodiments, the stress related condition is a psychosomatic disorder. In some embodiments, the psychosomatic disorder is selected from the group consisting of abdominal pain, allergy, asthma, blepharospasm, dysmenorrhea, essential hypertension, lower back pain, migraine and tension headaches, hyperhidrosis, irritable bowel syndrome, myofascial pain, pain, psychogenic emesis, Raynaud's disease, tinnitus, writer's cramp, and performance anxiety.

In some embodiments, the method or device is useful in rehabilitation therapy. In some embodiments, the rehabilitation therapy comprises rehabilitation of a subject suffering from a condition selected from the group consisting of causalgia, cerebral palsy, esophageal motility disorders, dysphagia, Guillain barre syndrome, hemiplegia, multiple sclerosis, neuromuscular reeducation, orthopedic recovery enhancement, paretic muscles, Parkinson's disease, post-cva rehabilitation, reduction of spasticity and hypertonicity, respiratory disorders, spinal cord injuries, stress management, stroke, tendon transfer, tic, and torticollis.

In some embodiments, the method or device is useful in the treatment of a condition which is at least partially unrelated to stress, the condition selected from the group consisting of acne, anger states, arthritis, attention deficit disorder, backache/neck pain, balance disorders, behavioral control (including addictions, such as alcohol addiction, drug addiction, nicotine addiction), bronchitis, bruxism, cardiac arrhythmia, cardiovascular disorders, carpal tunnel syndrome, chronic fatigue syndrome, chronic pain, concentration disorders, diabetes, dermatitis, cold extremities, digestive disorders, dysmenorrhea, eczema, endocrine disorders, epilepsy, fatigue, headaches, hyperhidrosis, hypertension, insomnia, impotence, incontinence, irritable bowel syndrome, labor pain, learning disabilities, mental fatigue, migraine, muscle aches, neck pain, poor concentration, postural dysfunction, rashes, respiratory disorders, sexual dysfunction, sleep disorders, sinus congestion, and ulcers.

In some embodiments, the method or device of the invention is useful in the treatment of addiction, such as substance addiction (for example, at least one of alcohol addiction, drug addiction, and nicotine addiction).

In some embodiments, the method or device is useful in the treatment of difficulties associated with dieting.

In some embodiments, the method or device of the invention is useful in performance and lifestyle applications, such as, for example, sports applications (improvement of performance in a sport), stress management, and voice-coaching.

Figure 1:
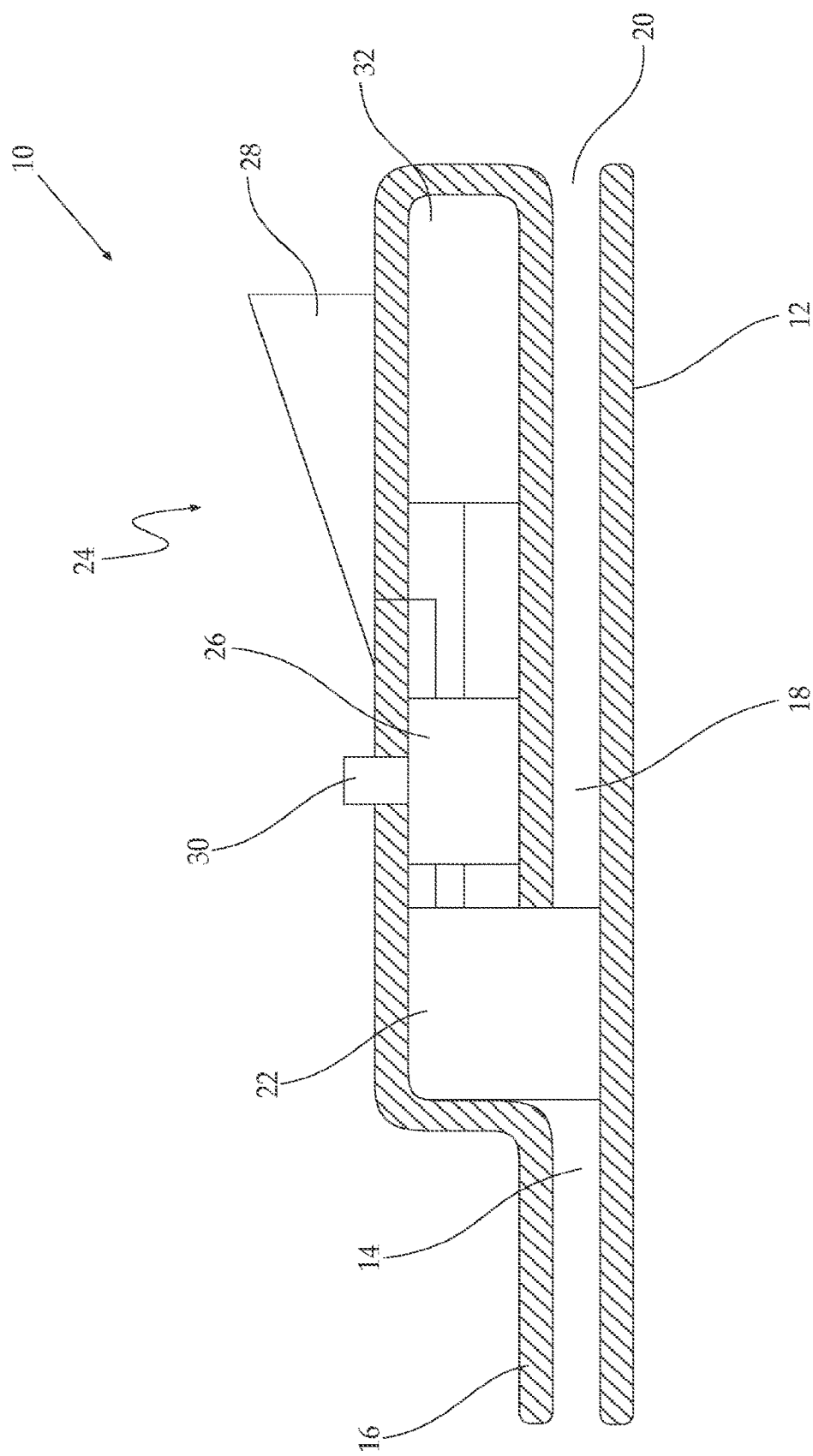
FIG. 1 depicts a cross-sectional representation of an embodiment of a device as taught herein, for determining exhalation duration and providing biofeedback.

Referring now to FIG. 1, a first embodiment of a device of the invention is schematically depicted, a device 10 comprising an elongated housing 12 configured (in terms of size, weight and shape) to be hand-held by a user, an exhalation inlet 14 for receiving exhaled breath of the user comprising a shaped mouthpiece 16 at the proximal end of housing 12 into which the user exhales, and an exhalation conduit 18 including an exhalation outlet 20 at the distal end of housing 12, configured so that exhaled breath received by exhalation inlet 14 passes through exhalation conduit 18 and exits to the surroundings through exhalation outlet 20.

Inside housing 12 are exhalation determiner 22 and components of a reporter 24 of device 10, including controller 26 (e.g., an integrated circuit or populated circuit board as known in the art), a display screen 28 (e.g., an LED or LCD screen), an on/off switch 30 and a power source 32 (e.g., a battery such as a Li-ion battery).

Exhalation determiner 22, is functionally associated with exhalation inlet 14 and is configured to determine when exhaled breath is received by exhalation inlet 14, and is configured to send one of two indications to controller 26 of reporter 24 associated with exhalation determiner 22: that exhaled breath is being received by exhalation inlet 14 or that exhaled breath is not being received by exhalation inlet 14. Specifically, in device 10, exhalation determiner 22 comprises a propeller. When exhaled breath is being received by exhalation inlet 14, the propeller rotates and an alternatingly on/off current is received by controller 26, corresponding to "exhalation". When exhaled breath is not being received by exhalation inlet 14, the propeller does not rotate and controller 26 receives either a continuous "on" signal or a continuous "off" signal, corresponding to "no exhalation".

Reporter 24 is associated with exhalation determiner 22 as noted above, and is configured to provide a visual signal related to an exhalation duration of exhaled breath received from exhalation determiner 22 to a user. The signal provided is provided as a comparison to a preferred "exhalation duration", for example five seconds. Specifically, when reporter 24 is activated, controller 26 generates instructions to display screen 28 showing a first column of ten illuminated blocks. When reporter 24 receives an "exhalation" signal from exhalation determiner 22, controller 26 generates instructions to display screen 28 to serially illuminate blocks of a second column parallel to the first column, from the bottom of the second column moving upwards, where a new block is illuminated every 0.5 seconds. Display screen 28 is located on an outer surface of housing 12 at a location which allows screen 28 to be clearly visible to the user during exhalation, with mouthpiece 16 in the mouth of the user.

A user who wants to use device 10 (for example, a person practicing meditation, or a person feeling the onset of a panic attack) places mouthpiece 16 in the mouth, activates device 10 by toggling switch 30 to the "on" position to activate exhalation determiner 22 and reporter 24 (including both controller 26 and display screen 28), and looks at display screen 28.

As long as switch 30 is at the "on" position, the first column of ten illuminated blocks is displayed on screen 28. When switch 30 is at the "off" position, screen 28 is turned off and the blocks of the first column are not displayed.

When the user exhales into exhalation inlet 14, the exhaled breath causes rotation of the propeller of exhalation determiner 22, producing an "exhalation" signal. Reporter 24 illuminates a new block in the second column of blocks every 0.5 seconds that an exhalation signal is continuously received from exhalation determiner 22. When ten blocks in the second column of blocks are illuminated on screen 28 (easily seen by the user looking at screen 28 with reference to the first column of ten illuminated blocks) the user knows that the exhalation duration has been 5 seconds that is sufficiently long and so inhales, preferably through the nose.

Whenever the user stops exhaling into exhalation inlet 14, the propeller of exhalation determiner 22, produces a "no exhalation" signal. Reporter 24 turns off illumination of all illuminated blocks in the second column. If exhalation is stopped prior to illumination of all the ten blocks in the second column of blocks, the user realizes that the exhalation duration in that breathing cycle was insufficiently long, and knows to make an effort to exhale for a longer duration in the following breathing cycle.

For a period of time, the user repeatedly exhales into exhalation inlet 14 while observing display screen 28 until a desired effect is achieved, e.g., inducing deep breathing, calming, overcoming panic.

Figure 2:
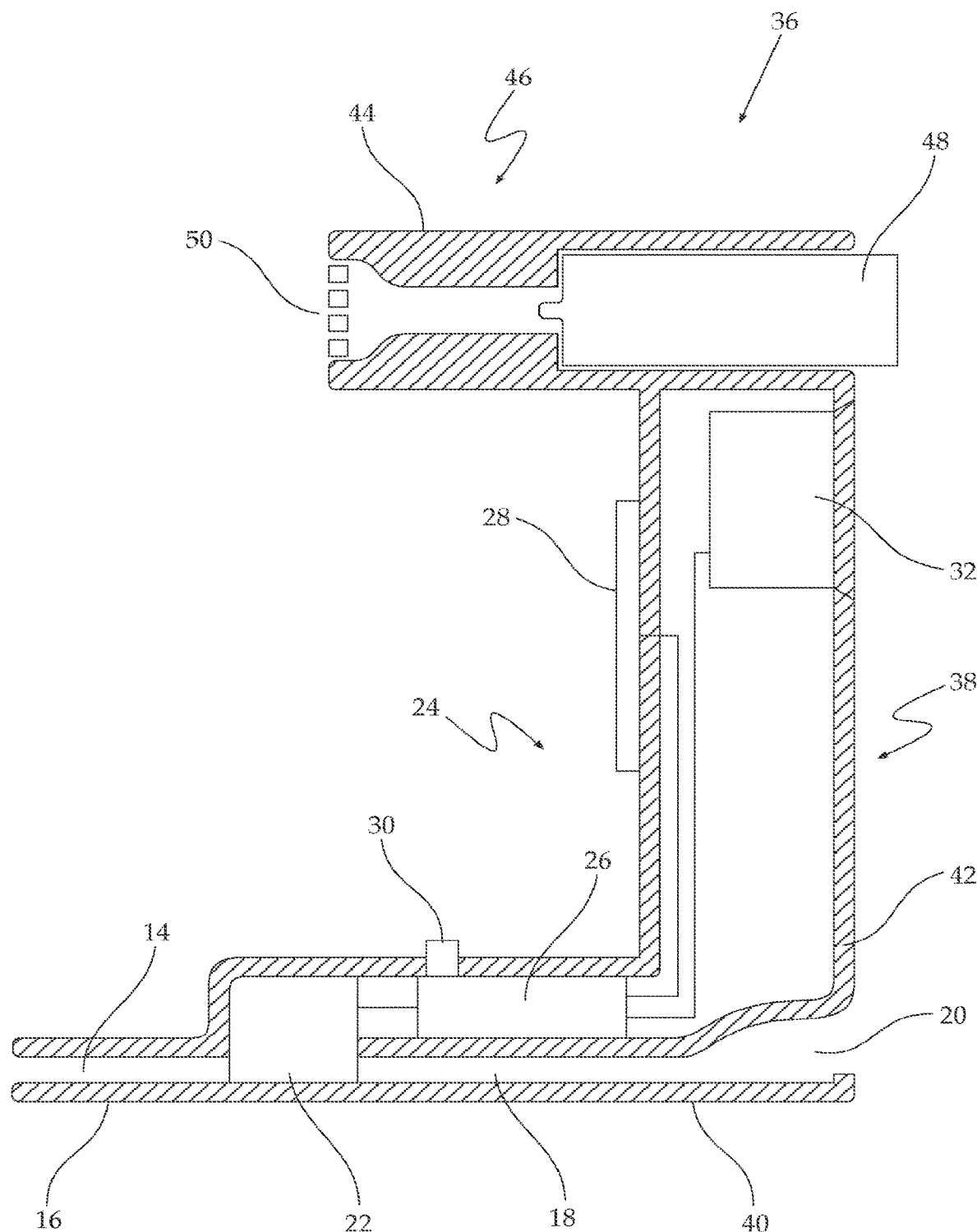
FIG. 2 depicts a cross-sectional representation of an embodiment of a device as taught herein, for determining exhalation duration, providing biofeedback and for dispensing an inhalable substance.

In FIG. 2, a second embodiment of a device of the invention is schematically depicted, a device 36 comprising a U-shaped housing 38 including a lower arm 40, a base portion 42 and an upper arm 44 configured (in terms of size, weight and shape) to be hand-held by a user, an exhalation inlet 14 for receiving exhaled breath of the user comprising a shaped mouthpiece 16 at the proximal end of lower arm 40 of housing 38 into which the user exhales, and an exhalation conduit 18 including an exhalation outlet 20 opening out in the middle of a base portion 42 of housing 38, configured so that exhaled breath received by exhalation inlet 14 passes through exhalation conduit 18 and exits to the surroundings through exhalation outlet 20.

As in device 10, physically associated with housing 38 are exhalation determiner 22 and components of a reporter 24 of device 10, including controller 26, a display screen 28, an on/off switch 30 and a power source 32, that are all mutually associated and function substantially as described above with reference to device 10.

Physically associated with upper arm 44 of device 36 is an inhalable substance dispenser 46 configured to dispense an inhalable substance such as an essential oil from an inhalable substance reservoir 48 through an inhalable substance outlet 50. In device 36, inhalable substance reservoir 48 is a plastic container in which is found cloth impregnated with neroli oil useful for relief of panic attacks.

Housing 38 is configured so that when exhalation inlet 14 is positioned by the user for receiving exhaled breath from the mouth of the user, inhalable substance outlet 50 is located in proximity of the nostrils of the nose of the user.

Inhalable substance reservoir 48 is configured to be reversibly functionally associated with inhalable substance dispenser 46. Such reversible functional association allows a user to use the same device but to select a suitable essential oil for a desired use.

Specifically, from the state depicted in FIG. 2 where inhalable substance reservoir 48 is functionally associated with inhalable substance dispenser 46, when desired, a user grasps a distal end of inhalable substance reservoir 48 and disconnects reservoir 48 from device 36 by pulling outwards so that there is no longer an inhalable substance reservoir 48 functionally associated with inhalable substance dispenser 46

From a state (not depicted) where no inhalable substance reservoir 48 is functionally associated with inhalable substance dispenser 46, a user can functionally associate a suitable inhalable substance reservoir 48. Specifically, a user functionally associates an inhalable substance reservoir 48 with inhalable substance dispenser 46 by pushing a suitable reservoir 48 into the opening in the distal end of upper arm 44 of housing 38 so that the reservoir is held in position, functionally associated with inhalable substance dispenser 46 by friction. The act of pushing the suitable reservoir into the distal opening opens a valve (e.g., a spring-loaded valve similar to a Schrader valve) at the terminal end of reservoir 48 allowing release of an inhalable substance contained therein.

Figure 3A:
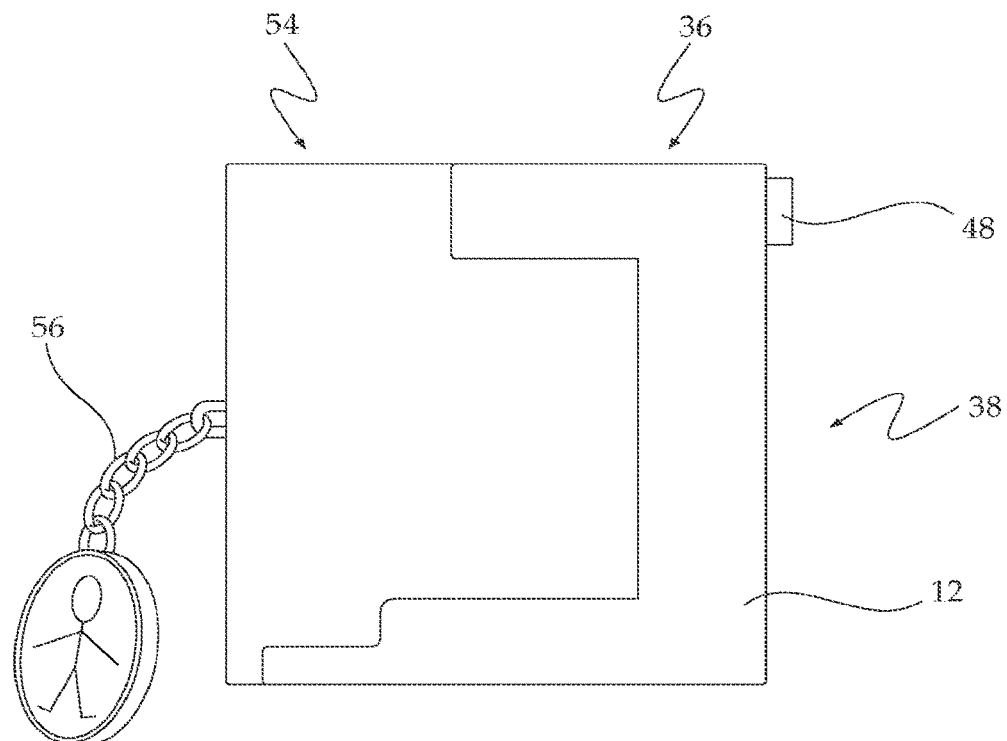
FIGS. 3A and 3B are schematic depictions of the device of FIG. 2, with a cover couplable to a housing of the device, with the cover coupled (FIG. 3A) and not-coupled (FIG. 3B)
Figure 3B:
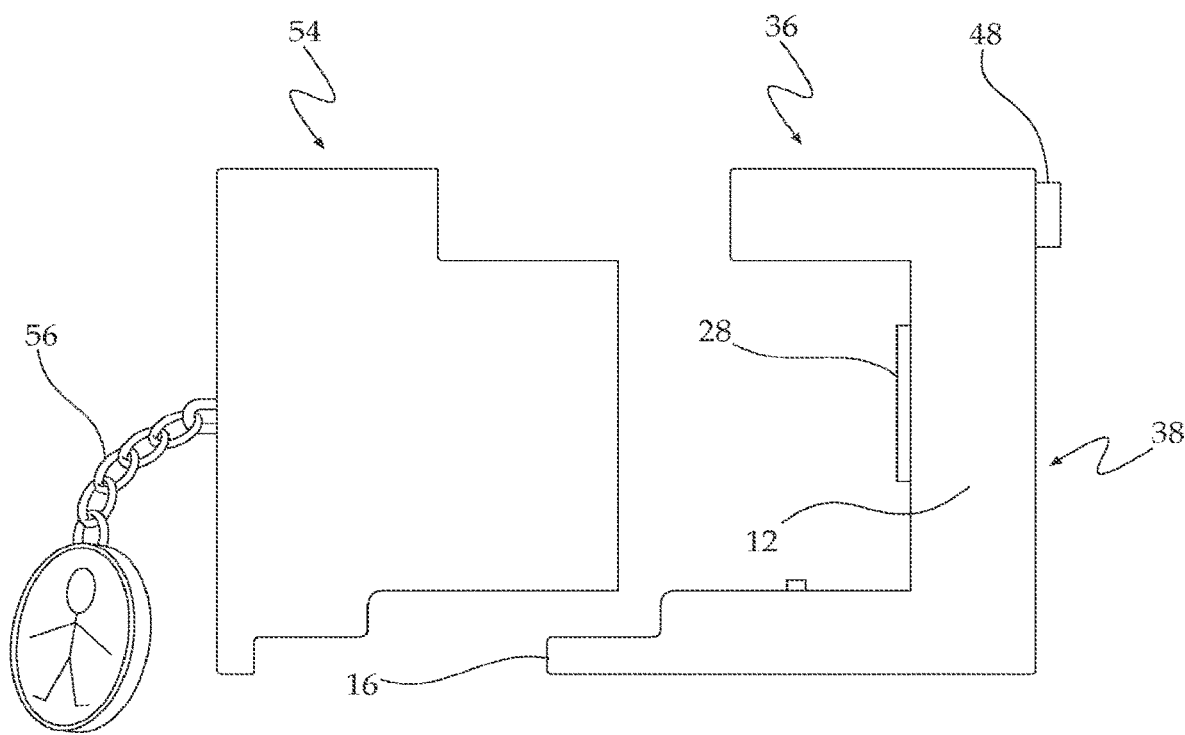

FIGS. 3A and 3B depict an embodiment of a device 36 of FIG. 2, further comprising a reversibly couplable cover 54 configured to reversibly couple to housing 38 of device 36. Cover 54 further comprises a tether 56 in the form of a keychain attached to an outer surface. When coupled to housing 38, FIG. 3A, cover 54 protects components of device 36 (e.g., display screen 28) from damage, substantially prevents entry of air into exhalation inlet 14, prevents escape of inhalable substance from inhalable substance outlet 50, assists in maintaining inlet 14, mouthpiece 16 and outlet 50 clean and keeps on/off switch 30 in an "off" state. When uncoupled from housing 38, FIG. 3B, device 36 is ready for use, including switch 30 toggling to an "on" state.

Device 36 discussed with reference to FIGS. 2 and 3 includes a U-shaped housing 38 having a lower arm 40 containing exhalation conduit 18 and an upper arm 44 containing inhalable substance dispenser 46 so that inhalable substance dispenser 46 is fixed to the rest of device 36. In some related embodiments, an upper arm 44 (in some embodiments, together with base portion 42 connecting upper arm 44 to lower arm 40) is reversibly detachable from lower arm 40. Such embodiments allow a user to optionally use the device with an inhalable substance dispenser or without an inhalable substance dispenser, in analogy to device 10.

Device 36 discussed with reference to FIGS. 2 and 3 includes an inhalable substance reservoir 48 that is configured to be reversibly functionally associated with an inhalable substance dispenser 46, allowing a user to change the nature of the inhalable substance dispensed by device 36. In some embodiments, an inhalable substance reservoir such as 48 is functionally associated, but not reversibly, with an inhalable substance dispenser such as 46 of a device. In some such embodiments, the device is provided with a specific inhalable substance and a user desiring a different inhalable substance must acquire a different device.

Device 36 discussed with reference to FIG. 3 includes a reversibly couplable cover 54: coupling cover 54 with housing 38 deactivating device 36 and uncoupling cover 54 from housing 38 activating device 36. In some embodiments, a device includes a cover that is not reversibly couplable. The cover is removed one-time, activating the device and thereafter the device is preferably discarded.

Figure 4A:
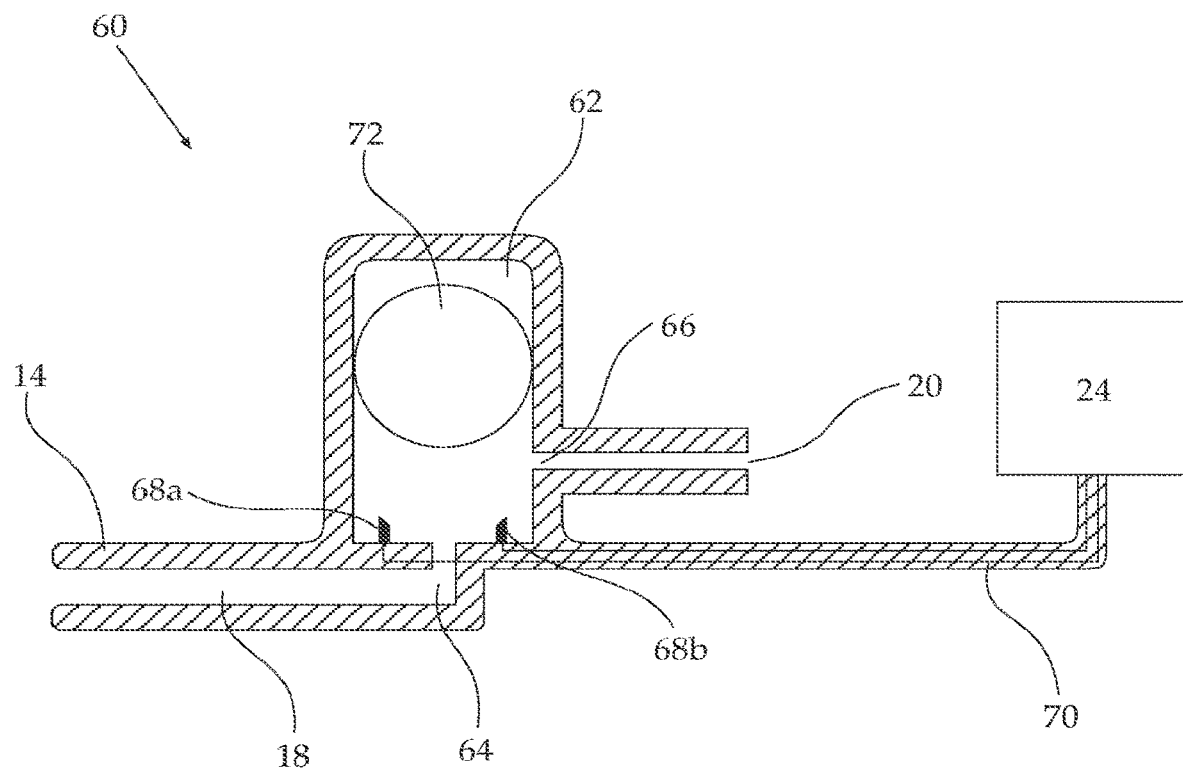
FIGS. 4A and 4B schematically depict, in cross section, an embodiment of an exhalation determiner useful in implementing some embodiments of the teachings herein, during exhalation (FIG. 4A) and during no exhalation (FIG. 4B)
Figure 4B:
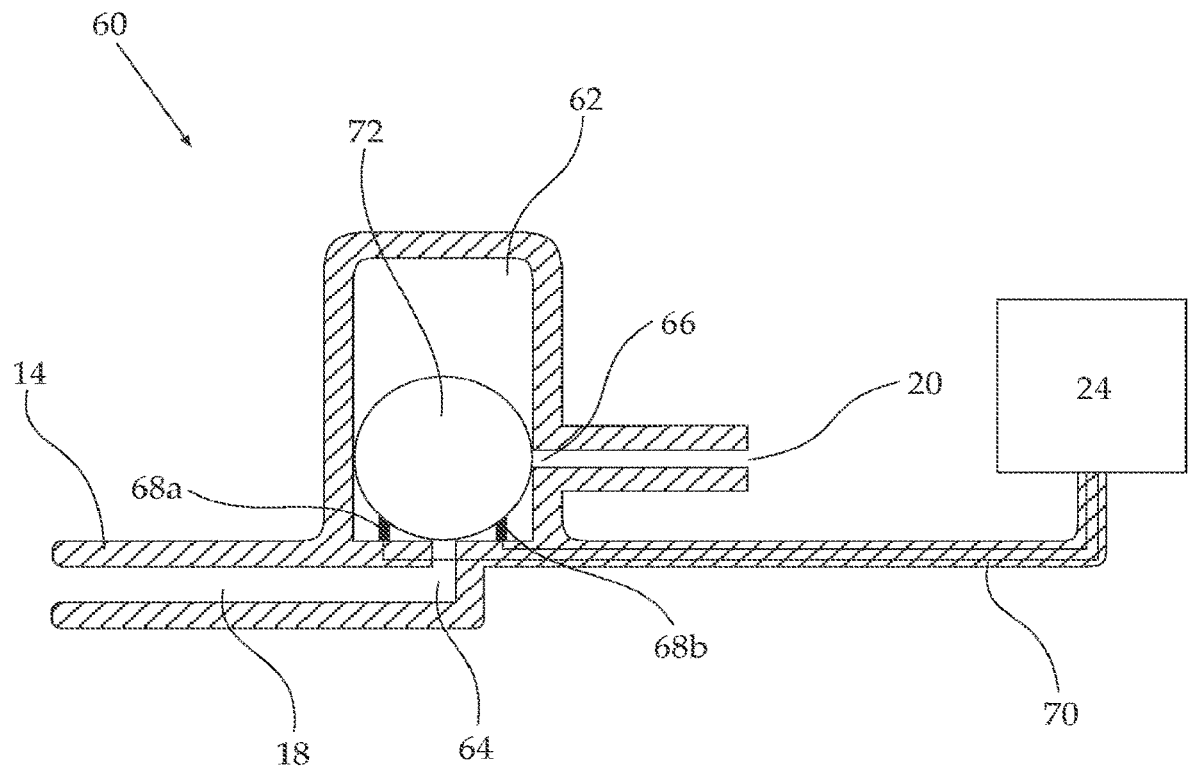

In FIGS. 4A and 4B is schematically depicted an additional embodiment of an exhalation determiner, exhalation determiner 60. Exhalation determiner 60 comprises a chamber 62 that constitutes a portion of an exhalation conduit 18 that is functionally associated with an exhalation inlet 14. Specifically, chamber 62 is in fluid communication with exhalation inlet 14 through lower opening 64 and is in fluid communication with exhalation outlet 20 through a side opening 66.

Flanking the sides of lower opening 64 are contacts 68a and 68b that are part of an electrical circuit 70 that is interrogatable by reporter 24.

Contained inside chamber 62 is a conductive ball 72, e.g., a polyethylene or celluloid ball on which outer surface a conductive layer of aluminum is deposited.

Exhalation determiner 60 is configured to determine when exhaled breath is received by exhalation inlet 14, and is configured to send one of two indications to reporter 24 associated with exhalation determiner 60: that exhaled breath is being received by exhalation inlet 14 or that exhaled breath is not being received by exhalation inlet 14. Specifically, when exhaled breath is being received by exhalation inlet 14, FIG. 4A, the exhaled breath enters chamber 62 through lower opening 64, lifting ball 72, and escaping chamber 62 through side opening 66. Electrical circuit 70 is broken, corresponding to an "exhalation" signal. When exhaled breath is not being received by exhalation inlet 14, FIG. 4B, ball 72 settles on contacts 68, closing electrical circuit 70, corresponding to a "no exhalation" signal.

Figure 5A:
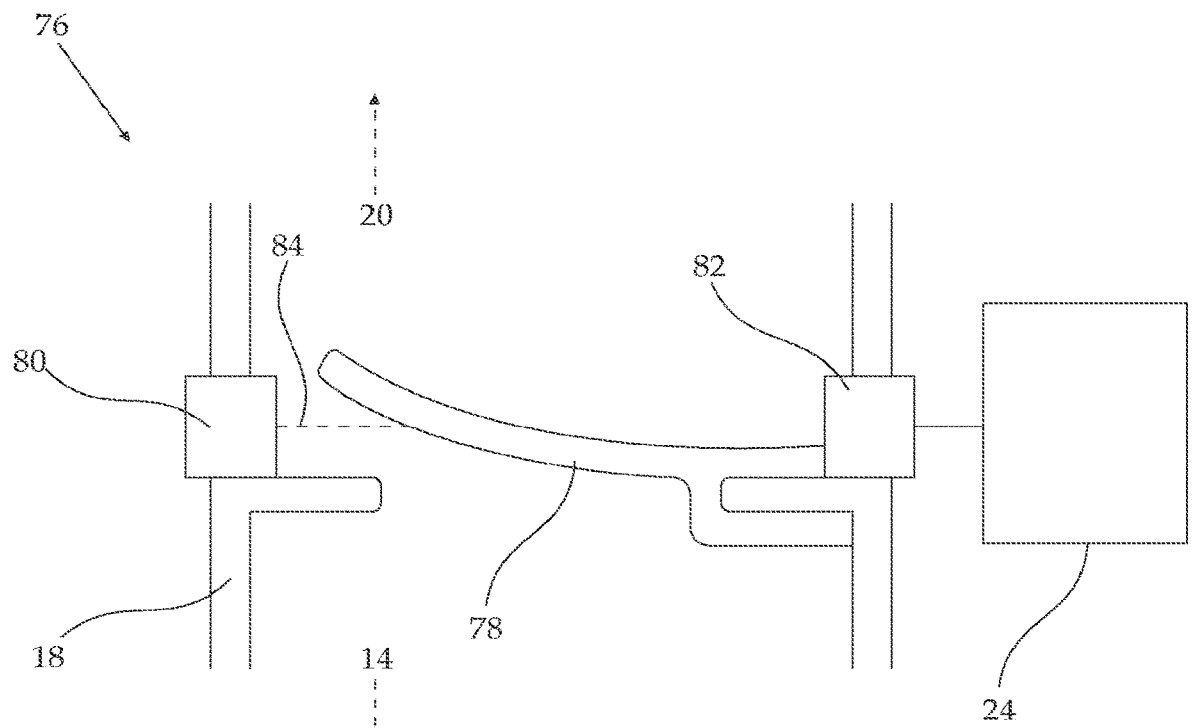
FIGS. 5A and 5B schematically depict, in cross section, an additional embodiment of an exhalation determiner useful in implementing some embodiments of the teachings herein, during exhalation (FIG. 5A) and during no exhalation (FIG. 5B)
Figure 5B:
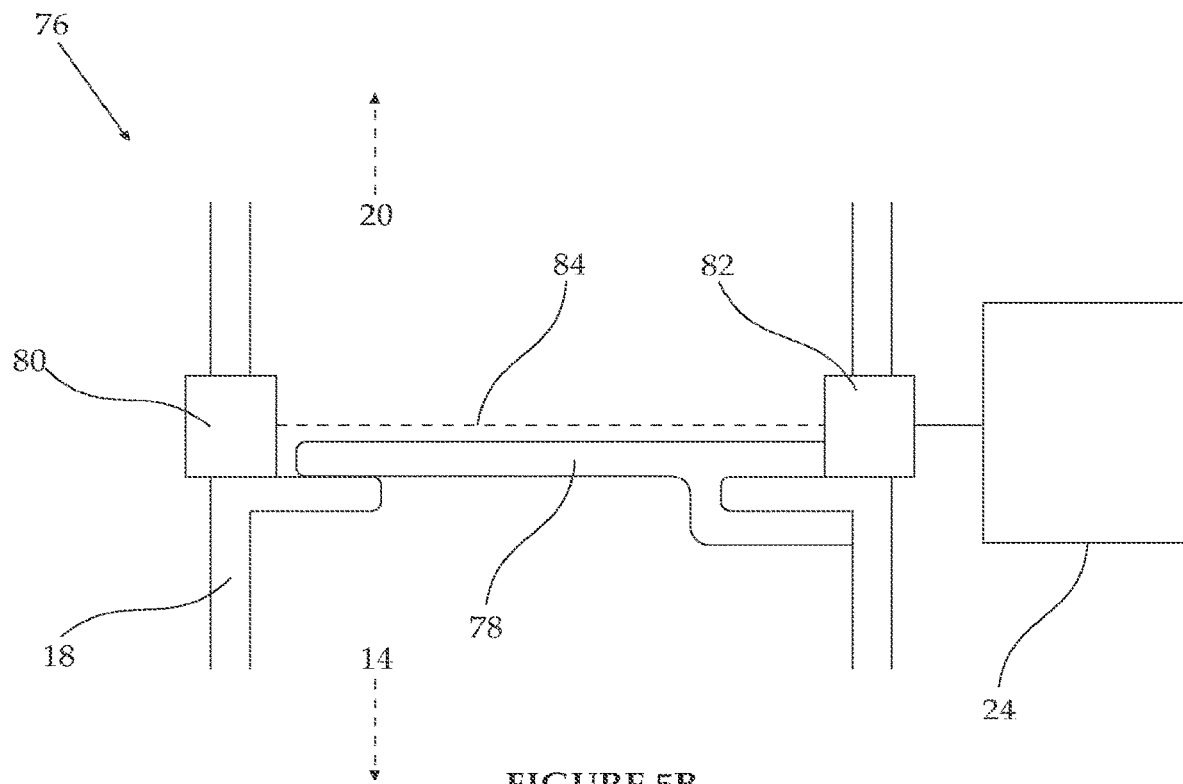

In FIGS. 5A and 5B is schematically depicted an additional embodiment of an exhalation determiner, exhalation determiner 76. Exhalation determiner 76 constitutes a portion of an exhalation conduit 18 and is thereby functionally associated with an exhalation inlet 14. Specifically, exhalation determiner 76 comprises a silicone rubber diaphragm 78 located inside exhalation conduit 18, configured to be biased in a "closed" position, blocking upstream fluid flow from exhalation outlet 20 towards exhalation inlet 14 through exhalation conduit 18. Located upstream from diaphragm 78, are a LED (Class I) laser 80 and a light detector 82. Laser 80 is configured, when activated, to produce a beam of light 84 that is projected just above and parallel to diaphragm 78 to be detected by detector 82. Detector 82 is functionally associated with reporter 24 and is configured to provide a signal to reporter 24 when a beam of light 84 is detected.

Exhalation determiner 76 is configured to determine when exhaled breath is received by exhalation inlet 14, and is configured to send one of two indications to reporter 24 associated with exhalation determiner 76: that exhaled breath is being received by exhalation inlet 14 or that exhaled breath is not being received by exhalation inlet 14. Specifically, when exhaled breath is being received by exhalation inlet 14, FIG. 5A, the exhaled breath passes downstream from exhalation inlet 14 towards exhalation outlet 20 through exhalation conduit 18, lifting diaphragm 78, blocking beam of light 84 from reaching detector 82, corresponding to an "exhalation" signal. When exhaled breath is not being received by exhalation inlet 14, FIG. 5B, diaphragm 78 closes, allowing beam of light 84 to reach detector 82, corresponding to a "no exhalation" signal.

Figure 6A:
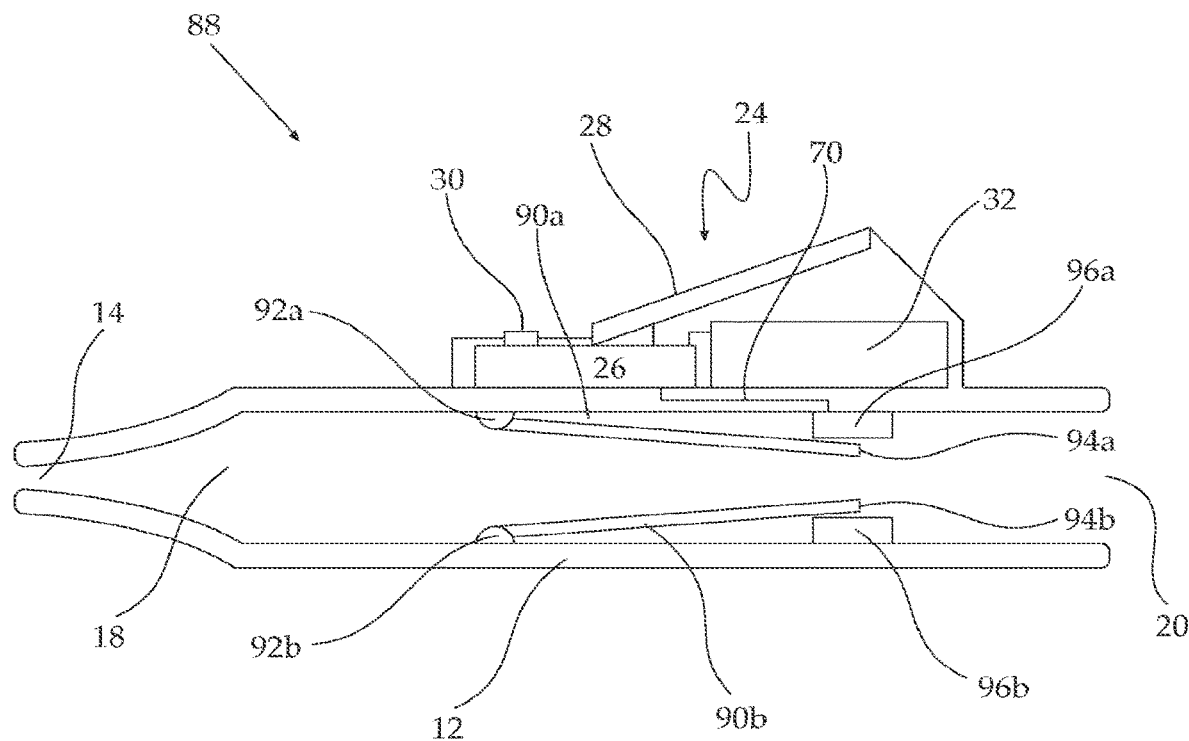
FIGS. 6A and 6B schematically depict, in cross section, an embodiment of a device as taught herein, including an additional embodiment of an exhalation determiner, during exhalation (FIG. 6A) and during no exhalation (FIG. 6B)
Figure 6B:
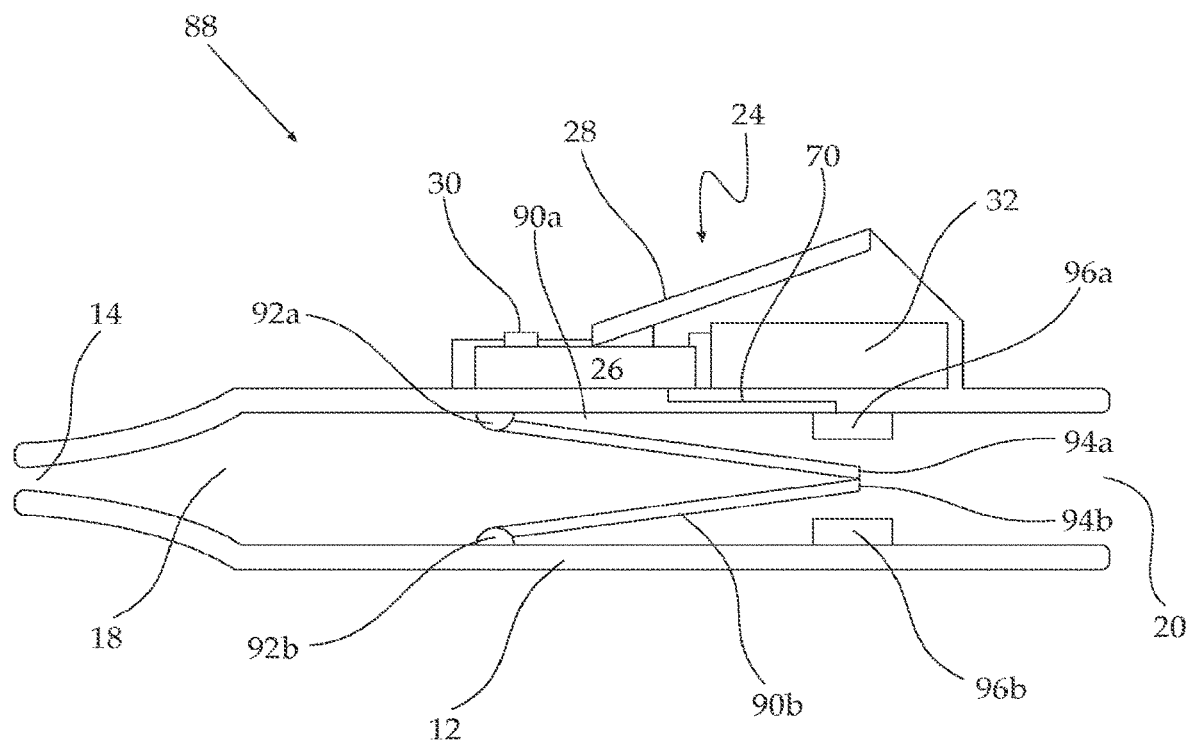

In FIGS. 6A and 6B is schematically depicted an additional embodiment of an exhalation determiner, exhalation determiner 88. Exhalation determiner 88 constitutes a portion of an exhalation conduit 18 (having a square cross section) and is thereby functionally associated with an exhalation inlet 14. Specifically, exhalation determiner 88 comprises two rigid reeds 90a and 90b rotatably mounted on respective axes 92a and 92b. Axes 92a and 92b are spring-loaded to be biased in a "closed" position where respective distal edges 94a and 94b are in mutual contact, blocking upstream fluid flow from exhalation outlet 20 towards exhalation inlet 14 through exhalation conduit 18. Downstream fluid flow of breath from exhalation inlet 14 to exhalation outlet 20 through exhalation conduit 18 applies a force that pivots reed 90b around axis 92b in a clockwise direction to contact a stop 96b and pivots reed 90a around axis 92a in a counterclockwise direction to contact a stop 96a. Stop 96a includes a microswitch that is part of an electrical circuit 70 that is interrogatable by reporter 24.

Exhalation determiner 88 is configured to determine when exhaled breath is received by exhalation inlet 14, and is configured to send one of two indications to reporter 24 associated with exhalation determiner 88: that exhaled breath is being received by exhalation inlet 14 or that exhaled breath is not being received by exhalation inlet 14. Specifically, when exhaled breath is being received by exhalation inlet 14, FIG. 6A, the exhaled breath passes through exhalation conduit 18, pivoting reed 90a to contact stop 96a, activating the microswitch that closes electrical circuit 70, corresponding to an "exhalation" signal. When exhaled breath is not being received by exhalation inlet 14, FIG. 6B, reed 90a rotates away from stop 96a, breaking electrical circuit 70, corresponding to a "no exhalation" signal.

As discussed above, in some embodiments a device as described herein comprises a flow-restrictor functionally associated with the exhalation conduit, configured for limiting the rate of flow of exhaled breath through the exhalation conduit. Such a flow-restrictor, typically defined by the cross-sectional area of some or all of the exhalation conduit, allows free flow of breath through the exhalation conduit at a relatively low (thus desirable) rate, but generates resistance to a too strong flow of breath through the exhalation conduit.

Exhalation determiner 60 depicted in FIG. 4 constitutes a flow-restrictor, specifically, the relatively small cross-sectional size of lower opening 64 and side opening 66 preventing a too strong flow of breath through exhalation conduit 18.

Exhalation determiner 76 depicted in FIG. 5 constitutes a flow-restrictor, specifically, the relatively small cross-sectional size of exhalation conduit 18 past diaphragm 78 preventing a too strong flow of breath through exhalation conduit 18.

Exhalation determiner 88 depicted in FIG. 6 constitutes a flow-restrictor, specifically, the relatively small cross-sectional size of exhalation conduit 18 past distal edges 94a and 94b of reeds 90a and 90b preventing a too strong flow of breath through exhalation conduit 18.

In some embodiments, the degree of flow-restriction of a flow-restrictor is adjustable. For example, in some embodiments related to exhalation determiner 88 depicted in FIG. 6, one or both of stops 96a and 96b are configured to be translated inwards and outwards of exhalation conduit 18, for example, in the manner of screws, thereby defining the distance between distal edges 94a and 94b of reeds 90a and 90b, and thereby the cross-sectional size of exhalation conduit 18.

As discussed above, in some embodiments a device as described herein comprises a one-way valve functionally associated with the exhalation conduit, configured for allowing downstream passage of exhaled breath from the exhalation inlet through the exhalation conduit and out through the exhalation outlet but for preventing upstream inhalation of air from the exhalation outlet, through the exhalation conduit and out through exhalation inlet to a user. Such a one-way valve assists a user in remembering to inhale through the nose, in some embodiments considered to be a "more correct" style of breathing.

Exhalation determiner 60 depicted in FIG. 4 constitutes such a one-way valve, specifically, ball 72 sealing lower opening 64 during potential upstream flow.

Exhalation determiner 76 depicted in FIG. 5 constitutes such a one-way valve, specifically, diaphragm 78 blocking exhalation conduit 18 during potential upstream flow.

Exhalation determiner 88 depicted in FIG. 6 constitutes such a one-way valve, specifically, reeds 90 blocking exhalation conduit 18 during potential upstream flow.

Figure 7C:
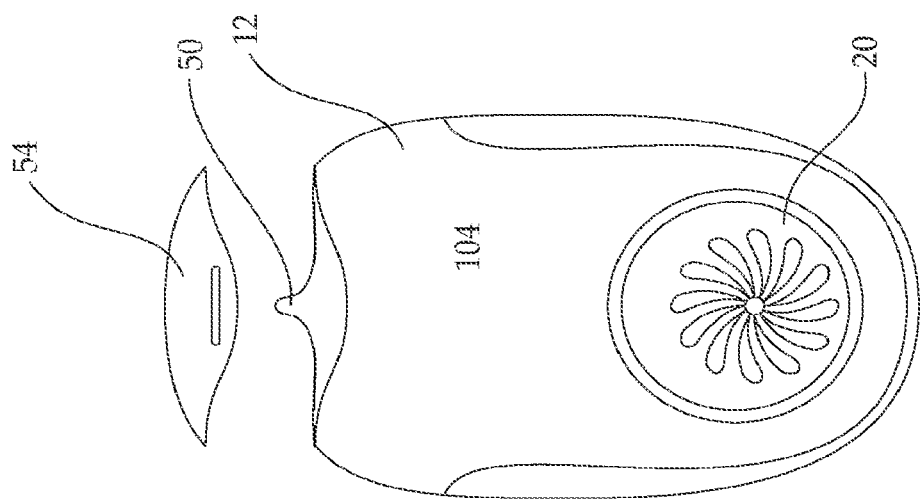
FIGS. 7A, 7B, 7C and 7D depict an embodiment of a device as taught herein in front view (FIG. 7A), side view (FIG. 7B) back view (FIG. 7C) and schematic side cross section (FIG. 7D.
Figure 7B:
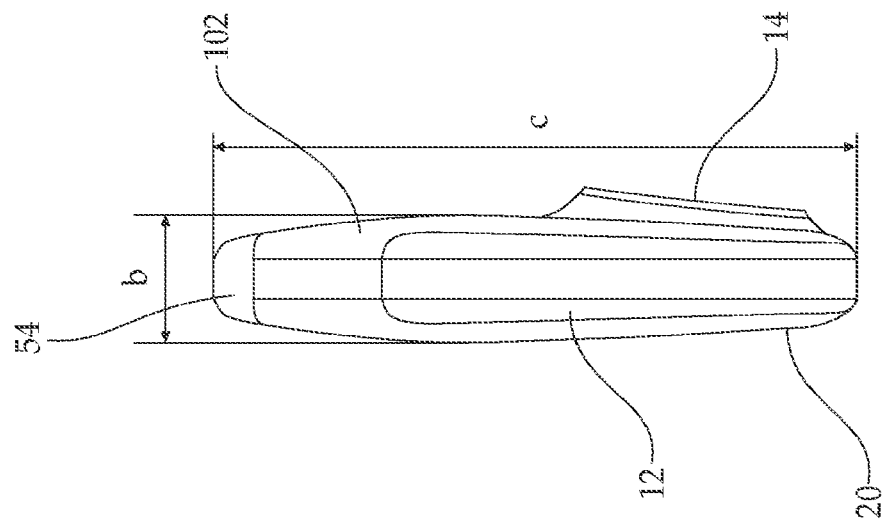
Figure 7A:
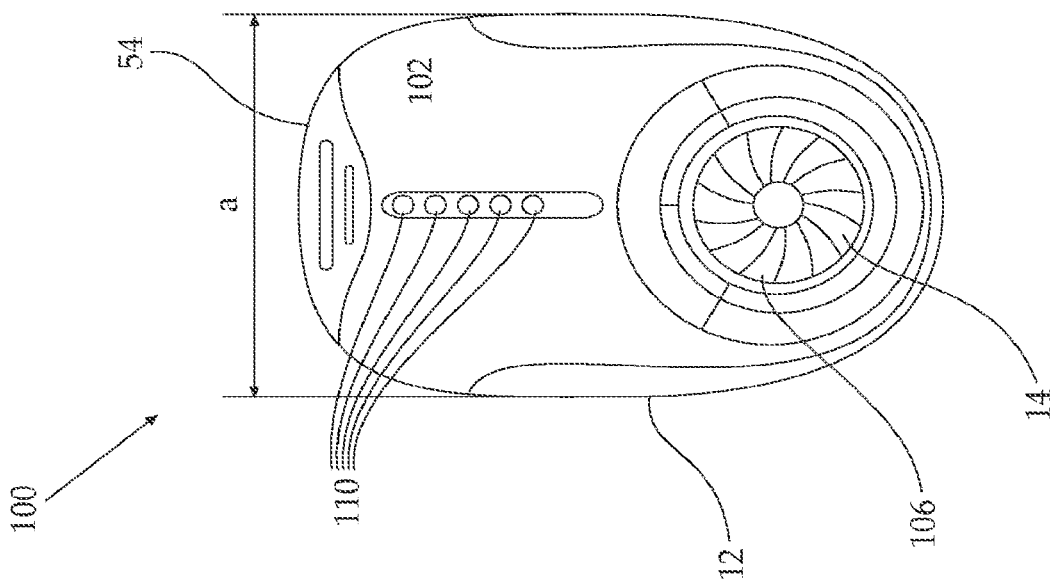
Figure 7D:
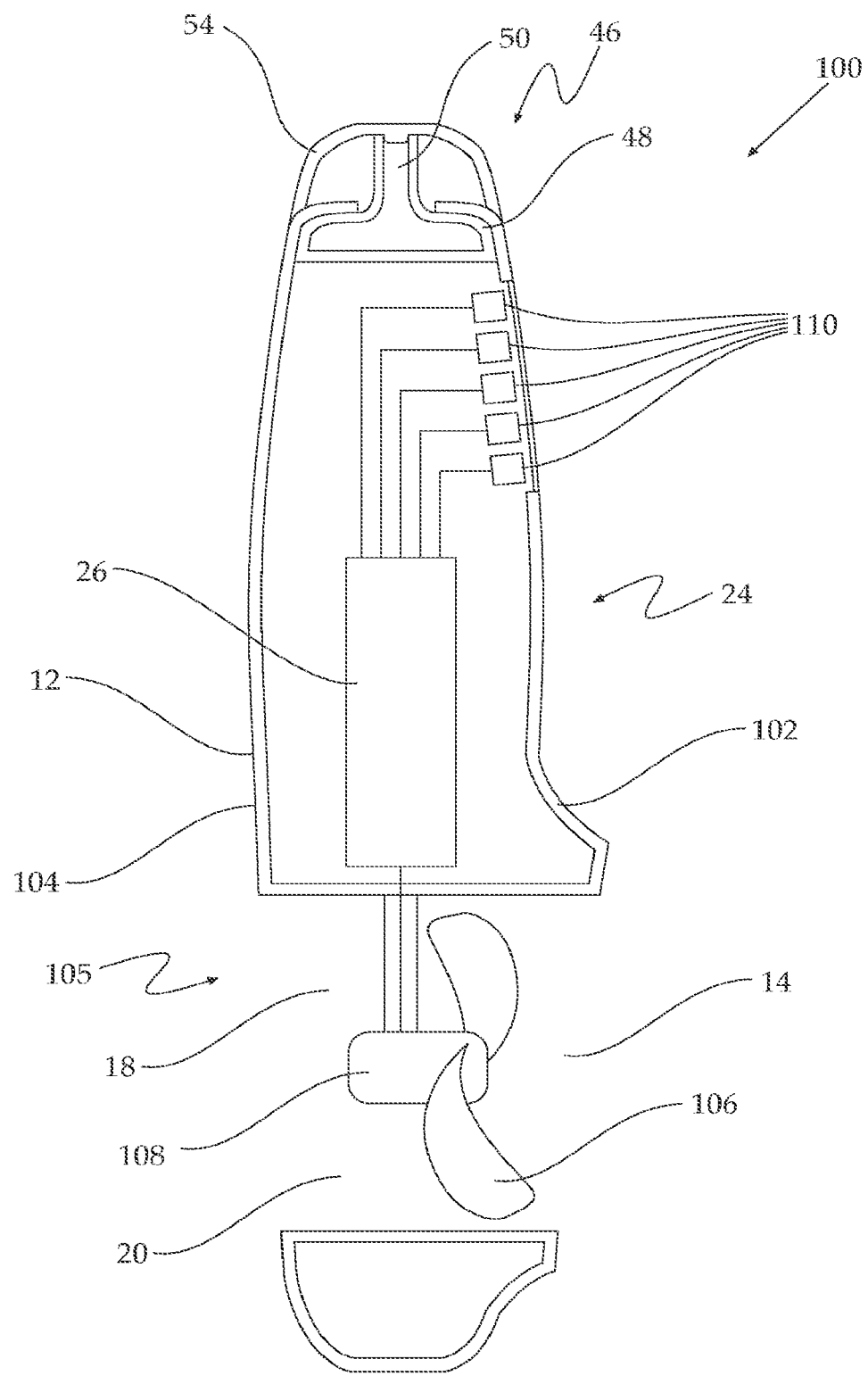

In FIGS. 7A to 7D an additional embodiment of a device as described herein is depicted, device 100, in front view (FIG. 7A), side view (FIG. 7B), back view (FIG. 7C) and schematic cross section (FIG. 7D). Device 100 includes a flattened housing 12 that is 50 mm wide (a), 15 mm thick (b)

and 75 mm high (c) with a front face 102 including an exhalation inlet 14, a back face 104 with an exhalation outlet 20 and an exhalation conduit 18 therebetween. Device 100 includes an inhalable substance dispenser 46, including an inhalable substance reservoir 48 (a container) holding an essential oil. Inhalable substance outlet 50 (the neck of reservoir 48) is reversibly sealable with cover 54.

An exhalation determiner 105 of device 100 comprises a propeller 106 functionally associated with an electrical generator 108. A reporter 24 of device 100 comprises a processor 26 (an integrated circuit) and five light-emitting diodes 110 arranged in a vertical column and visible through front face 102 of housing 12. Device 100 is devoid of an on/off switch and of a power source.

For use, a user holds device 100 with exhalation inlet 14 in proximity of the mouth. The user exhales into exhalation inlet 14, so that the exhaled breath passes through exhalation conduit 18 and out through exhalation outlet 20. The exhaled breath passing through exhalation conduit 18 causes propeller 106 to rotate, causing generator 108 to generate electricity. The generated electricity powers processor 26. With detection of generated electricity (and power up), processor 26 times the duration of exhalation and successively lights light-emitting diodes 110 from the lowest to the highest, one a second. The user knows that to achieve the desired five-second exhalation duration, it is necessary to exhale long enough so that all five light-emitting diodes 110 are lit.

If desired, during use the user can remove cover 54 so that inhalable substance outlet 50 is located in the proximity of the nostrils. In such a way, the user can inhale the inhalable substance that volatilizes and escapes inhalable substance reservoir 48. When desired, the user can reseal inhalable substance outlet 50 with cover 54.

Figure 8C:
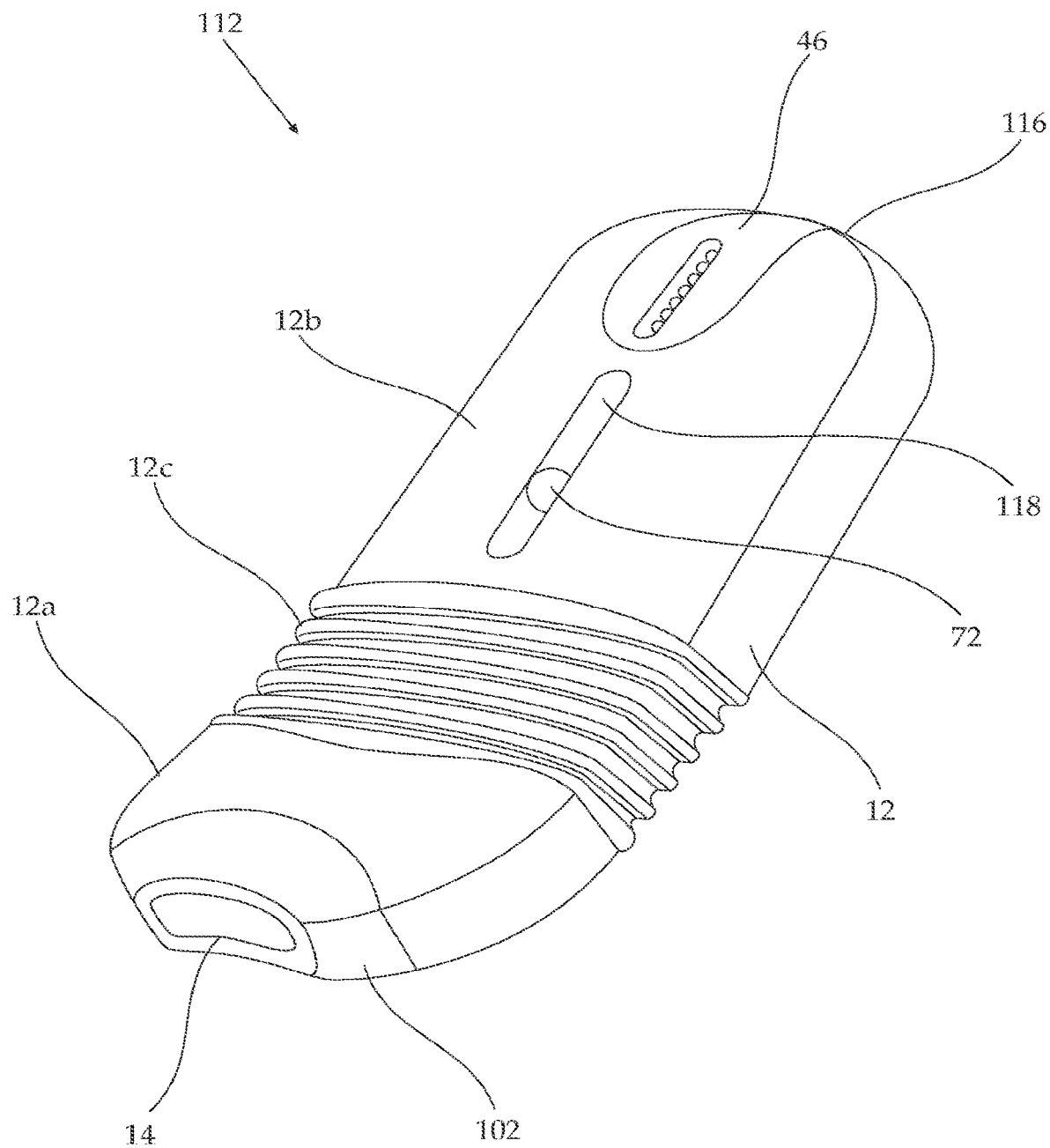

In FIGS. 8A to 8C an additional embodiment of a device as described herein is depicted, device 112 in front view (FIGS. 8A and 8B), and perspective view during use (FIG. 8C). Device 112 includes a flattened housing 12 50 mm wide (a), 10 mm thick and 80 mm high (c) with a proximal end 102 including an exhalation inlet 14, a distal end 116 with an exhalation outlet 20 and an exhalation conduit 18 therebetween.

Housing 12 is articulated, including two rigid sections of polycarbonate, proximal section 12a and distal section 12b, mutually connected by articulated middle section 12c of silicone rubber.

Contained inside distal section 12b is an exhalation determiner similar to exhalation determiner 60 depicted in FIGS. 4A and 4B, including a conductive ball 72 that is raised when exhaled air passes through a exhalation conduit. The reporter of device 112 includes ball 72 that is visible through a window 118 in housing 12. Additionally, there is a lamp that is lit by a controller of device 112 when a desired exhalation duration is attained.

Device 112 includes an inhalable substance dispenser 46, including an inhalable substance reservoir (a fibrous pad impregnated with an essential oil). Inhalable substance dispenser 46 is a component separate from housing 12 that is provided in a sealed aluminized sachet and is configured to reversibly engage the rim of exhalation outlet 20.

For use, a user holds device 112 with exhalation inlet 14 in proximity of the mouth and bends housing 12 upwards around articulated middle section 12c so that window 118 is visible and exhalation outlet 20 is close to the nostrils. As the user exhales, the exhalation duration is determined as described hereinabove with reference to exhalation determiner 60. If desired, the user removes an inhalable substance dispenser 46 from a sachet and places in exhalation outlet 20 and can inhale released inhalable substance. Exhaled air passes through the exhalation reservoir, helping volatilize the inhalable substance in the inhalable substance reservoir.

Figure 9B:
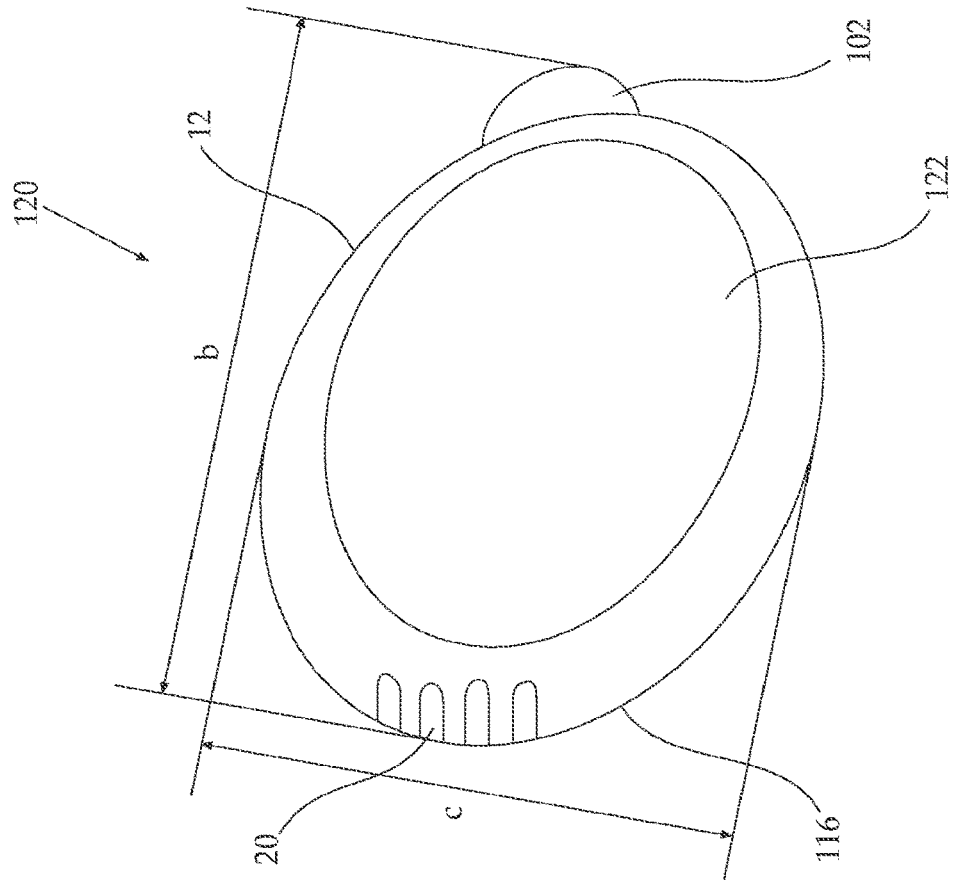
FIGS. 9A and 9B depict an embodiment of a device as taught herein in perspective view from the front somewhat angled to the right side (FIG. 9A) and from the left side somewhat angled to the back (FIG. 9B)
Figure 9A:
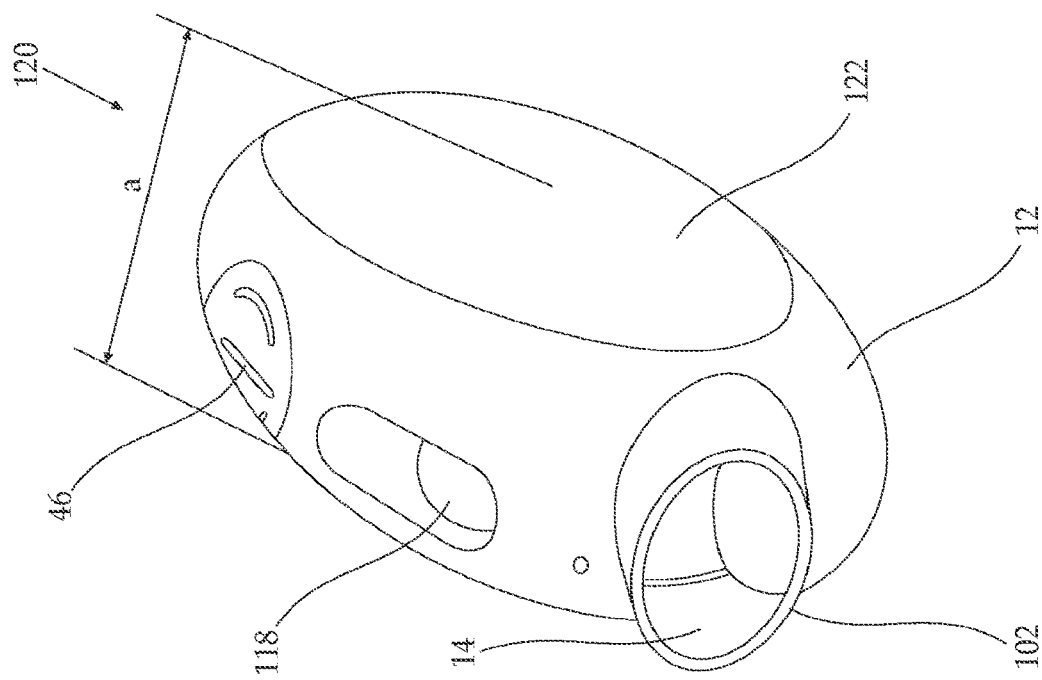

In FIGS. 9A to 9B an additional embodiment of a device as described herein is depicted, device 120, in perspective view from the front somewhat angled to the right side (FIG. 9A) and from the left side somewhat angled to the back (FIG. 9B). Device 120 includes an elongated rounded housing 12, 36 mm wide (a), 73 mm long (b) and 55 mm high (c) with a proximal end 102 including an exhalation inlet 14, a distal end 116 with an exhalation outlet 20 and an exhalation conduit 18 therebetween. Housing 12 is rigid but includes two pads 122 of silicone rubber.

Contained inside housing 12 is an exhalation determiner similar to exhalation determiner 22 of device 10 depicted in FIG. 1, comprising a propeller (not depicted) that rotates when exhaled breath passes through the exhalation conduit. In device 120, the axis of rotation of the propeller is parallel to the width (dimension a), in the manner of a waterwheel. The propeller is visible through a window 118. The processor of device 120 is configured to determine when the propeller rotates and when not, and is thereby configured to determine an exhalation duration. When exhalation duration is sufficiently long, the processor triggers vibrating elements functionally associated with pads 122 so that a user knows when a desired exhalation duration is attained.

Device 120 includes an inhalable substance dispenser 46, including an inhalable substance reservoir 48 (a fibrous pad impregnated with an essential oil). Inhalable substance dispenser 46 is a component separate from housing 12 that is provided in a sealed aluminized sachet and is configured to reversibly engage a cavity in the top portion of housing 12.

For use, a user holds device 120 with exhalation inlet 14 in proximity of the mouth so that window 118 is visible and a substance dispenser 46 is close to the nostrils. As the user exhales, the exhalation duration is determined as described hereinabove with reference to exhalation determiner 22. Through window 118, the user sees that the propeller rotates and feels the vibration of pads 122 when a desired exhalation duration is attained.

In FIGS. 10A to 10D an additional embodiment of a device as described herein is depicted, device 124, in a closed configuration (FIG. 10A), in a partially-open configuration (FIG. 10B), in a fully-open configuration (FIG. 10C) and schematically (FIG. 10D). Device 124 comprises a housing 12 made of two rigid housing parts 12a and 12b mutually joined, in the manner of a codex, with a hinge 126, a portion of an inner cover 128 (a sheet of elastomer such as silicone rubber).

When housing 12 is in a closed configuration (FIG. 10A), housing parts 12a and 12b are close together, folding inner cover 128 in half so that inner cover 128 is contained between housing parts 12a and 12b. A microswitch 30 functionally associated with a controller 26 of device 124 is depressed, maintaining controller 26 and device 124 in an inactive "OFF" state, suitable for storage and transport When housing 12 is in an open configuration (FIGS. 10B and 10C), housing parts 12a and 12b are spaced apart and inner cover 128 is exposed. Microswitch 30 is not depressed, so that controller 26 and device 124 are in an active "ON" state in a state ready to provide biofeedback to a user.

The exhalation inlet of device 124 is an area 130 of inner cover 128 visibly marked with both a symbol and letters. Underneath area 130 of inner cover 128 are located components of an exhalation determiner 132 comprising two temperature sensors 134 (e.g., thermistors) and two pressure sensors 136 (e.g., piezoelectric elements) functionally associated with controller 26. A reference temperature sensor 138 is positioned underneath inner cover 128 remote from area 130.

A reporter 24 of device 124 comprises two substantially identical groups 24a and 24b, each of six light-emitting diodes 110 arranged in columns underneath inner cover 128, light-emitting diodes functionally associated with controller 26.

Device 124 also includes an inhalable substance dispenser 46, a slot-shaped volume inside inner cover 128 configured to removably hold a suitable inhalable substance reservoir 48, a flexible flat component of cardboard or paper impregnated with an inhalable substance such as an essential oil. Inhalable substance dispenser 46 is in fluid communication with the surroundings through inhalable substance outlets, openings in inner cover 128. Device 124 is configured so that when area 130 of inner cover 128 is positioned close to the mouth of a human user, the inhalable substance outlets are located in proximity of nostrils of the user.

Before use (immediately before or a significant time before, e.g. a few hours before), a user places a fresh inhalable substance reservoir 48 in inhalable substance dispenser 46. As long as device 124 is in a closed configuration (FIG. 10A), device 124 is inactive and inhalable substance does not substantially volatilize from inhalable substance reservoir 48.

For use, a user moves housing parts 12a and 12b apart (FIG. 10B and FIG. 10C). As microswitch 30 is no longer depressed, device 124 is in an active state. Inhalable substance from inhalable substance reservoir 48 volatilizes and is released into the surroundings. The user holds device 124 so that area 130 of inner cover 128 is positioned close to the mouth, bringing the inhalable substance outlets in proximity of the nostrils and enjoying the advantages of inhaling the substance.

The user exhales through the mouth. During an exhalation, temperature sensors 134 report the warmth of detected exhaled breath and pressure sensors 136 report the pressure of detected exhaled breath to controller 26. Controller 26 identifies an exhalation by identifying a transient temperature difference between the ambient temperature reported by reference temperature sensor 138 and temperature sensors 134 that temporally correlates with an increased pressure reported by pressure sensors 136.

As long as the user exhales, controller 26 serially activates light-emitting diodes of columns 24a and 24b, a new diode each 0.8 seconds, as a visual biofeedback related to the exhalation duration. When the person stops exhaling, the concomitant lower temperature reported by temperature sensors 134 and the concomitant decreased pressure reported by pressure sensors 136 is considered to be non-exhalation, so controller 26 extinguishes all the activated light-emitting diodes of columns 24a and 24b. The user is able to take advantage of the biofeedback to control the duration, and consequently rate, of breathing in accordance with the teachings herein.

In some non-depicted embodiments related to device 124, a device includes only temperature sensors 134 and no pressure sensors 136. In some non-depicted embodiments related to device 124, a device includes only pressure sensors 136 and no temperature sensors 134. In some non-depicted embodiments related to device 124, a device including temperature sensors 134 is devoid of a reference temperature sensor 138.

It is important to note that in some embodiments, an inhalable substance reservoir is replaceable. In some embodiments, an inhalable substance reservoir is not replaceable: when such an inhalable substance reservoir is spent, the device is either discarded or used without the advantageous effects of an inhalable substance. In some embodiments, an inhalable substance reservoir of a device as described herein is for a single use: after one use, the reservoir is spent. In some embodiments, an inhalable substance reservoir of a device as described herein is for multiple uses: the reservoir is spent after a number of uses. In some embodiments, a reservoir is configured to be spent after between a week and a few months of being used for the first time.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

Citation or identification of any reference in this application shall not be construed as an admission that such reference is available as prior art to the invention.

What is claimed is:

1. A biofeedback device comprising:
an inlet for receiving exhaled breath from a user's mouth;
a determiner physically associated with a device housing, the determiner functionally associated with the inlet, the determiner configured to determine when the exhaled breath is received by the inlet;
a reporter associated with the determiner, the reporter configured to determine an actual exhalation duration of the exhaled breath and to provide a signal to the user;
an inhalable substance outlet; and
a dispenser associated with the inhalable substance outlet, the dispenser configured to dispense an inhalable substance to the user through the inhalable substance outlet,
wherein the signal comprises a comparison of the actual exhalation duration to a preferred exhalation duration.

2. The device of claim 1, wherein the inlet is functionally associated with a conduit having an outlet.

3. The device of claim 2, wherein the inlet is configured such that the exhaled breath passes from the inlet through the conduit and exiting through the outlet.

4. The device of claim 1, wherein the device housing is configured to be held by the user while the inlet receives the exhaled breath.

5. The device of claim 1, wherein both the inhalable substance outlet and the dispenser are physically associated with the housing, and wherein the conduit is contained within the housing.

6. The device of claim 1, wherein the housing is configured such that, when the inlet receives the exhaled breath, the inhalable substance outlet is located in proximity of the user's nostrils.

7. The device of claim 1, further comprising:
an inhalable substance reservoir configured to store the inhalable substance and to release the inhalable substance to the dispenser.

8. The device of claim 1, wherein the signal is a visual and/or audible signal defined by the user, and wherein the device further comprises one or more data ports for downloading and/or uploading the visual and/or audible signal.

9. A biofeedback device comprising:
an inlet for receiving exhaled breath from a user's mouth;
a determiner physically associated with a device housing, the determiner functionally associated with the inlet, the determiner configured to determine when the exhaled breath is received by the inlet;
a reporter associated with the determiner, the reporter configured to:
determine an actual exhalation duration of the exhaled breath,
compare the actual exhalation duration to a preferred exhalation duration, and
provide a signal to the user indicating whether the actual exhalation duration is less than, substantially equal to, or greater than the preferred exhalation duration; and
a one-way valve functionally associated with the conduit, the one-way valve configured to allow passage of the exhaled breath from the inlet through the outlet and out through the outlet, the one-way valve further configured to prevent inhalation of air from the outlet, through the outlet, and out through the outlet.

10. The device of claim 9, wherein the inlet is functionally associated with a conduit having an outlet, and wherein the inlet is configured such that the exhaled breath passes from the inlet through the conduit and exiting through the outlet.

11. The device of claim 9, wherein the device housing is configured to be held by the user while the inlet receives the exhaled breath.

12. The device of claim 9, wherein the determiner is configured to function as the one-way valve.

13. The device of claim 9, wherein the device is configured to allow the user to set a target exhalation duration through a user interface, wherein the target exhalation duration is determined by the results of a previous use of the device.

14. The device of claim 9, wherein the device is further configured to decrease a target threshold when receiving a first exhaled breath if an exhalation duration of the first exhaled breath is less than the target threshold and to increase the target threshold when receiving the first exhaled breath if the exhalation duration of the first exhaled breath is greater than the target threshold.

15. The device of claim 9, wherein the determiner comprises circuitry for determining when the exhaled breath is received by the inlet.

16. A biofeedback device comprising:
an inlet for receiving exhaled breath from a user's mouth;
a determiner physically associated with a device housing, the determiner functionally associated with the inlet, the determiner configured to determine when the exhaled breath is received by the inlet;
a reporter associated with the determiner, the reporter configured to (i) determine an actual exhalation duration of the exhaled breath received from the determiner, and (ii) provide a signal to the user; and
a one-way valve configured to allow passage of exhaled breath from the inlet through a conduit and out through an outlet, the one-way valve further configured to prevent inhalation of air from the outlet, through the conduit, and out through the inlet,
wherein the signal comprises a comparison of the actual exhalation duration to a preferred exhalation duration.

17. The device of claim 16, wherein the actual exhalation duration of the exhaled breath is obtained by determining presence of flow through the conduit by:
a propeller, rotated by the exhaled breath, providing an electrical signal to the reporter, and/or
an electrical circuit connected to the reporter, the electrical circuit comprising an electrical switch activated by the exhaled breath providing a closed electrical circuit when there is no exhalation, and an open electrical circuit during exhalation, and/or
an opto-interrupter comprising a LED, a light detector connected to the reporter, and a blocking element configured to enable passage of light from the LED to the light detector when there is no exhalation, and to block passage of light from the LED to the light detector during exhalation, and/or
one or more temperature sensors connected to the reporter which detect a temperature change caused by exhaled breath, and/or
one or more pressure sensors connected to the reporter which detect a pressure change caused by exhaled breath.

18. The device of claim 16, further comprising:
a flow restrictor associated with the conduit, the flow restrictor configured to limit flow rate of the exhaled breath through the conduit above a predetermined or an adjustable rate.

* * * * *